US009427233B2

(12) United States Patent
Fearnot et al.

(10) Patent No.: US 9,427,233 B2
(45) Date of Patent: Aug. 30, 2016

(54) VASCULAR OCCLUSION DEVICES AND METHODS

(75) Inventors: Neal E. Fearnot, West Lafayette, IN (US); Michael E. Leckrone, Lafayette, IN (US)

(73) Assignee: Cook Medical Technologies, LLC, Bloomington, IN (US)

( * ) Notice: Subject to any disclaimer, the term of this patent is extended or adjusted under 35 U.S.C. 154(b) by 929 days.

(21) Appl. No.: 13/489,970

(22) Filed: Jun. 6, 2012

(65) Prior Publication Data

US 2012/0310269 A1    Dec. 6, 2012

Related U.S. Application Data

(60) Provisional application No. 61/493,595, filed on Jun. 6, 2011.

(51) Int. Cl.
*A61M 29/00* (2006.01)
*A61B 17/12* (2006.01)
*A61L 31/00* (2006.01)
(Continued)

(52) U.S. Cl.
CPC ..... *A61B 17/12022* (2013.01); *A61B 17/1219* (2013.01); *A61B 17/12109* (2013.01); *A61B 17/12177* (2013.01); *A61L 31/005* (2013.01); *A61L 31/146* (2013.01); *A61L 31/16* (2013.01); *A61L 31/18* (2013.01); *A61B 17/1215* (2013.01); *A61B 17/12031* (2013.01); *A61B 17/12145* (2013.01); *A61B 17/12168* (2013.01); *A61B 17/12172* (2013.01); *A61B 2017/00004* (2013.01); *A61B 2017/00778* (2013.01); *A61B 2017/00853* (2013.01); *A61B 2017/00871* (2013.01); *A61B 2017/00889* (2013.01); *A61B 2017/00893* (2013.01); *A61B 2017/00898* (2013.01); *A61B 2017/1205* (2013.01);
(Continued)

(58) Field of Classification Search
CPC .................. A61B 17/12022; A61B 17/12031; A61B 17/12109; A61B 17/1215; A61B 17/12168; A61B 17/12177
See application file for complete search history.

(56) References Cited

U.S. PATENT DOCUMENTS 5,674,198 A * 10/1997 Leone ....................... 604/101.05
6,143,015 A * 11/2000 Nobles ............. A61B 17/12036
                                                604/96.01
(Continued)

OTHER PUBLICATIONS

International Search Report and Written Opinion issued in PCT/US2012/041108, dated Mar. 26, 2013.

*Primary Examiner* — Julie A Szpira
(74) *Attorney, Agent, or Firm* — Woodard Emhardt Moriarty McNett & Henry LLP

(57) ABSTRACT

The present invention provides, in certain embodiments, unique products and methods for occluding vascular vessels. Implantable devices useful in some inventive embodiments include at least two expandable occluding members, e.g., self-expandable sponge form devices, with an intermediate segment extending between the members. These devices are preferably compressible for placement in a delivery device lumen for delivery to a vascular vessel site. Upon deployment in the vessel, each of the members expands to occlude the vessel at a separate vessel location with the intermediate segment occupying space in the vessel between the two members. Optionally, the intermediate segment can be constructed to provide a hollow or other interior region for receiving one or more materials, for example, to receive an injectable fill material after one or both of the expandable members have been deployed.

38 Claims, 9 Drawing Sheets

(51) Int. Cl.
   *A61L 31/14*   (2006.01)
   *A61L 31/16*   (2006.01)
   *A61L 31/18*   (2006.01)
   *A61B 17/00*   (2006.01)
   *A61M 25/06*   (2006.01)

(52) U.S. Cl.
   CPC ....... *A61L2300/418* (2013.01); *A61L 2430/36* (2013.01); *A61M 2025/0681* (2013.01)

(56) References Cited

U.S. PATENT DOCUMENTS

| | | | |
|---|---|---|---|
| 6,689,097 B2 * | 2/2004 | Thramann | 604/96.01 |
| 2003/0153935 A1 | 8/2003 | Mialhe | |
| 2006/0149309 A1 | 7/2006 | Paul | |
| 2006/0161197 A1 | 7/2006 | Paul | |
| 2009/0018637 A1 | 1/2009 | Paul, Jr. | |
| 2010/0106178 A1 * | 4/2010 | Obermiller et al. | 606/194 |

* cited by examiner

VASCULAR OCCLUSION DEVICES AND METHODS

REFERENCE TO RELATED APPLICATION

This application claims the benefit of U.S. Provisional Application No. 61/493,595, filed Jun. 6, 2011, entitled Vascular Occlusion Devices and Methods, which is hereby incorporated by reference.

BACKGROUND

The present invention relates generally to medical technology and in particular aspects to devices and methods for occluding vascular vessels.

As further background, there are a variety of reasons why it is desirable to occlude or otherwise modify fluid flow through vascular vessels and other openings and passageways in the body. A vessel might be occluded, for example, to treat an aneurysm, AV fistula, incompetent venous valve or other blood vessel complication. Vascular vessels are comprised of tissue and are the conduit for circulating blood through a mammalian body. A vascular vessel that carries blood from the heart is known as an artery. A vascular vessel that returns blood to the heart is known as a vein. There are three types of veins in a human: deep veins, which are located deep in the body close to the bones, superficial veins, which are located close to the skin, and perforating veins, which are smaller veins that connect the deep veins to the superficial veins.

To assist blood flow, venous vascular vessels contain venous valves. Each venous valve is located inside the vein and typically includes at least two valve leaflets, which are disposed annularly along the inside wall of the vein. These leaflets open to permit blood flow toward the heart and close, upon a change in pressure, such as a transition from systole to diastole, to restrict the back flow of blood. When blood flows towards the heart, the venous pressure forces the valve leaflets to move apart in a downstream flexing motion, thereby creating an open path for blood flow. The leaflets normally flex together when moving in the upstream direction; therefore, they return to a closed position to restrict or prevent blood flow in the upstream, or retrograde, direction after the venous pressure is relieved. The leaflets, when functioning properly, extend radially inward toward one another such that the leaflet tips, or cusps contact each other when the valve is closed.

On occasion, and for a variety of reasons, such as congenital valve or vein weakness, disease in the vein, obesity, pregnancy, and/or an occupation requiring long periods of standing, one or more valves in a vein will allow deleterious retrograde flow to occur. When a valve allows such retrograde flow, blood will collect, or pool in vessels beneath the valve. This pooling of blood causes an increase in the venous pressure below the valve. Venous valves that allow such deleterious retrograde flow are known as incompetent or inadequate venous valves. The condition resulting from such incompetent venous valves is known as venous valve insufficiency.

In the condition of venous valve insufficiency, the venous valve leaflets do not function properly. Incompetent venous valves can cause the veins to bulge, can cause swelling in the patient's lower extremities, and can result in varicose veins and/or chronic venous insufficiency. If left untreated, venous valve insufficiency can cause venous stasis ulcers of the skin and subcutaneous tissue.

A common method of treatment for venous valve insufficiency is the placement of an elastic stocking around the patient's leg to apply external pressure to the vein, forcing the walls radially inward to force the leaflets into apposition. Although sometimes successful, the tight stocking is quite uncomfortable, especially in warm weather, because the stocking must be constantly worn to keep the leaflets in apposition. The elastic stocking also affects the patient's physical appearance, thereby potentially having an adverse psychological affect. This physical and/or psychological discomfort can lead to the patient removing the stocking, thereby inhibiting treatment.

Surgical methods for treatment of venous valve insufficiency have also been developed. A vein with incompetent venous valves can be surgically constricted to bring incompetent leaflets into closer proximity in hopes of restoring natural valve function. Methods for surgical constriction of an incompetent vein include implanting a frame around the outside of the vessel, placing a constricting suture around the vessel (e.g., valvuloplasty), or other types of treatment to the outside of the vessel to induce vessel contraction. Other surgical venous valve insufficiency treatment methods include bypassing or replacing damaged venous valves with autologous sections of veins containing competent valves.

Another surgical method includes vein stripping and ligation. In this procedure, the femoral vein and other major venous tributaries are disconnected from the greater saphenous vein (GSV) and tied off. Next, the GSV is removed from the leg by advancing a wire through the vein, tying the wire to a saphenous vein end, and then pulling the wire, and vein, out through an incision in the upper calf or ankle. Unfortunately, the above surgeries require at least one incision and have several undesirable side effects and risks, such as a long patient recovery time, the potential for scarring, and numerous other risks inherent with surgery, such as those associated with the administration of anesthesia.

Recently, various implantable prosthetic devices and minimally invasive methods for implantation of these devices have been suggested to treat venous valve insufficiency. Such prosthetic devices can be inserted intravascularly, for example from an implantation catheter. Prosthetic devices can function as a replacement venous valve, or enhance venous valve function by bringing incompetent valve leaflets into closer proximity. In one procedure, venous valve function can be enhanced by clipping the valve leaflets together with a clip made from a biocompatible material, such as a metal or polymer.

Recently, a number of methods have been suggested to treat varicose veins and venous valve leaflets with energy sources, such as radiofrequency (RF) energy. In one such method, valve leaflets can be fastened together with electrodes delivering RF energy. In another such method, a catheter having an electrode tip can be used to apply RF energy to cause localized heating and corresponding shrinkage of venous tissue. After treatment of one venous section is complete, the catheter can be repositioned to treat a different venous section. Other known disruption techniques involve the use of laser energy such as with endovenous laser therapy (EVLT).

Methods for treatment of varicose veins have also been developed involving various forms of sclerotherapy. Generally, sclerotherapy involves the delivery of one or more sclerosing agents to the lumen of a varicose or other small diameter vein, which induce the vein to collapse and the venous walls to fuse, thereby closing the vein.

There remain needs for improved and/or alternative techniques, devices and systems for modifying vascular vessels. The present disclosure is addressed to those needs.

SUMMARY

The present invention provides, in certain aspects, unique products and methods for occluding vascular vessels. One such product includes a vascular implant that is suitable for transluminal vascular delivery to a vascular vessel site. This implant includes a first expandable member, and a second expandable member that is spaced from the first expandable member. Each of these members is compressible to permit delivery through the vasculature to the vascular vessel site, and expandable at the site to block flow through the vessel. In certain forms, the expandable members will be equipped to expand when no longer held in a compressed condition, e.g., upon deployment from a delivery device lumen. The implant further includes an intermediate segment which extends between the first expandable member and the second expandable member, and includes an interior region for possible receipt of a fill material. Accordingly, in some embodiments, the product will also include a fill material that can be used to fill at least part of this interior region.

Another inventive product for occluding a vascular vessel includes an implant having a first end portion, a second end portion and a wall of material extending therebetween so as to provide a fillable implant body between the first end portion and the second end portion. The first end portion includes a first expandable member, and the second end portion includes a second expandable member. Each of these members is compressible to permit transluminal vascular delivery to a vascular vessel site, and expandable at the site so as to position the respective end portions in the vessel to block flow through the vessel. In some forms, at least one of the expandable members incorporates a frame or frame-like component (e.g., a Nitinol frame).

In a further embodiment, a medical product for occluding a vascular vessel includes a vascular implant that is suitable for transluminal vascular delivery to a vascular vessel site. The implant includes a tubular segment, a first expandable occluding member, and a second expandable occluding member. The tubular segment has a first end and a second end, and includes a wall that is formed with a compliant sheet material. The sheet material is harvested from a collagenous tissue source, and the tubular segment is deliverable to a vascular vessel site for lining an interior wall of the vessel. The first occluding member is attached to the tubular segment at or near its first end, and the second occluding member is attached to the tubular segment at or near its second end. Each of these occluding members is compressible to permit delivery through the vasculature, and expandable in a vascular vessel to occlude the vessel. Optionally, this product also includes an endoluminally advanceable delivery device that has a lumen, and in such instances, the vascular implant is removably positionable in the delivery device lumen, and deployable therefrom in a vascular vessel.

An additional aspect of the present invention provides a method for occluding a vascular vessel. In this method, a vascular implant that is suitable for transluminal vascular delivery to a vascular vessel site is provided. This implant includes a first expandable member, a second expandable member and an intermediate segment extending therebetween. The intermediate segment includes an interior region for receipt of a fill material. Each of the expandable members is compressible to permit delivery through the vasculature to the vascular vessel site, and expandable at the site to block flow through the vessel. In one step, the vascular implant is delivered to the vascular vessel site such that the first expandable member and the second expandable member expand to block flow through the vessel. In another step, a fill material for filling the interior region of the intermediate segment is provided, and thereafter at least part of the interior region is filled with the fill material. In one embodiment, the implant is removably positioned in a lumen of a delivery device. Thereafter, the delivery device is located in the vascular vessel, and the implant is deployed from the delivery device lumen.

Another inventive method for occluding a vascular vessel includes providing an endoluminally advanceable delivery device and a vascular implant. The delivery device has a lumen communicating with a distal open end, and further has an expandable cuff located at or near its distal end. The vascular implant is removably positioned in the delivery device lumen, and is configured for deployment from the delivery device lumen in the vascular vessel for occluding the vessel. The implant includes a first expandable occluding member, and a second expandable occluding member that is spaced from the first occluding member. Each of these members is effective to expand upon removal from the delivery device lumen in the vascular vessel so as to occlude the vessel. The implant further includes an implant body which occurs between the first occluding member and the second occluding member. In one step, the delivery device is located in a vascular vessel. Thereafter, the expandable cuff is expanded so as to occlude the vessel at a first vessel location. In another step, the first occluding member is deployed from the delivery device lumen such that the first occluding member expands and occludes the vessel at a second vessel location that is spaced from the first vessel location, thereby forming an intermediate vessel segment between the first location and the second location. The intermediate vessel segment will generally contain blood, and in a further step, all or part of this blood is evacuated from the intermediate vessel segment through the delivery device lumen. In another step, the second occluding member is deployed from the delivery device lumen such that the second occluding member expands and occludes the vessel at a third vessel location occurring between the first vessel location and the second vessel location.

Other objects, embodiments, forms, features, advantages, aspects, and benefits of the present disclosure shall become apparent from the detailed description and drawings included herein.

DETAILED DESCRIPTION

Figure 1:
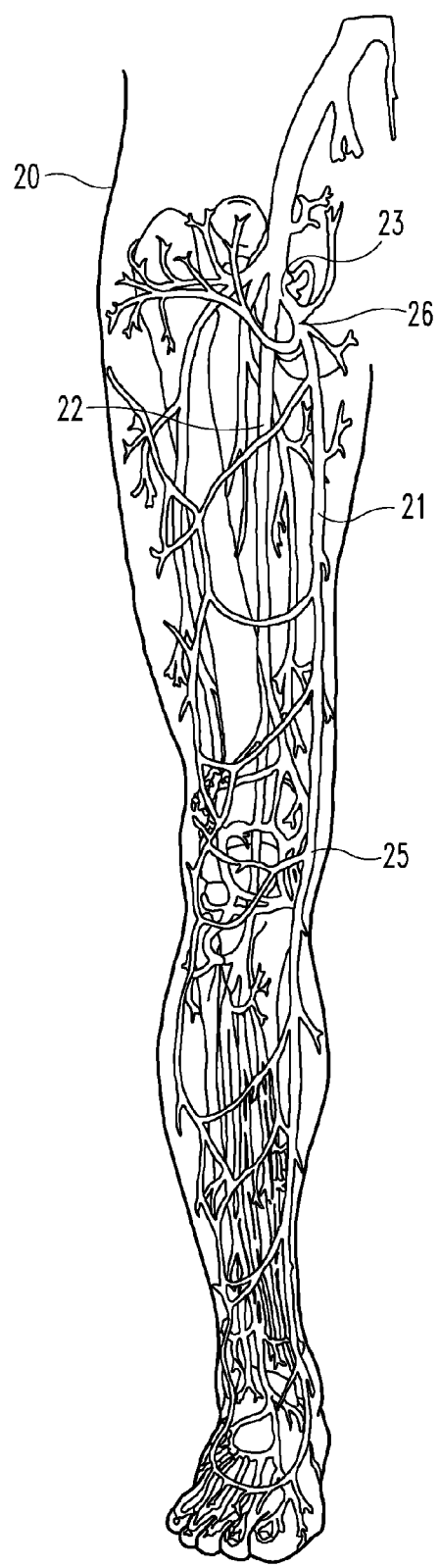
FIG. 1 depicts a human leg showing certain venous structures therein.

While the present invention may be embodied in many different forms, for the purpose of promoting an understanding of the principles of the present invention, reference will now be made to the embodiments illustrated in the drawings, and specific language will be used to describe the same. It will nevertheless be understood that no limitation of the scope of the invention is thereby intended. Any alterations and further modifications in the described embodiments and any further applications of the principles of the present invention as described herein are contemplated as would normally occur to one skilled in the art to which the invention relates.

As disclosed above, in certain aspects, the present invention provides unique products and methods for occluding vascular vessels. In some forms, useful implantable devices will include a first expandable member, a second expandable member and an intermediate component extending between the members. In other forms, the implantable devices may include a first expandable member and a fillable component extending therefrom, and, optionally a second expandable member connected to the fillable component, e.g. at or near an opposite end of the fillable component from the first expandable member. Advantageously, the implant can be compressed or otherwise compacted for placement in a delivery device for transluminal vascular delivery to a vascular vessel site. When deployed, the at least one expandable member or each of the expandable members can be caused or allowed to expand in the vessel so as to occlude the vessel at a separate vessel location, either by itself or in conjunction with one or more other devices and/or materials. In this regard, in some forms, a first occluding component can occlude the vessel at a first vessel location, and a second occluding component can occlude the vessel at a second vessel location, with the intermediate component occupying a space in the vessel between the first and second occlusions. In certain embodiments, the intermediate component or fillable component will include a sheet or other material that is adapted to provide a hollow or otherwise fillable interior space into which one or more substances, materials, etc. can be placed prior to deployment and/or after at least part of the implant has been deployed. In some preferred forms, all or part of the implant will comprise a remodelable material such that the patient's tissue can remodel the implant to enhance and promote occlusion of the vessel.

Inventive products and methods can be used to affect various passageways and openings in the body including those in the vasculature. With reference now more particularly to the figures, shown in FIG. 1 is a diagram of a human leg 20 showing certain venous structures therein. In particular, shown is human leg 20 having GSV 21 and femoral vein 22 which adjoin at the sapheno-femoral junction 23. In accordance with certain aspects of the present invention, the GSV 21 can be treated in a region constituting any or all of the passage between a point 25 occurring near the medial side of the knee to a point 26 occurring prior to the sapheno-femoral junction 23. Desirably, such treatment will be effective to prevent reflux of venous blood from the sapheno-femoral junction 23 in a direction down toward the medial side of the knee (e.g. at point 25). Such occlusion is effective to treat varicosities that commonly occur in lower portions of the leg, e.g. portions occurring below the knee.

Figure 2:
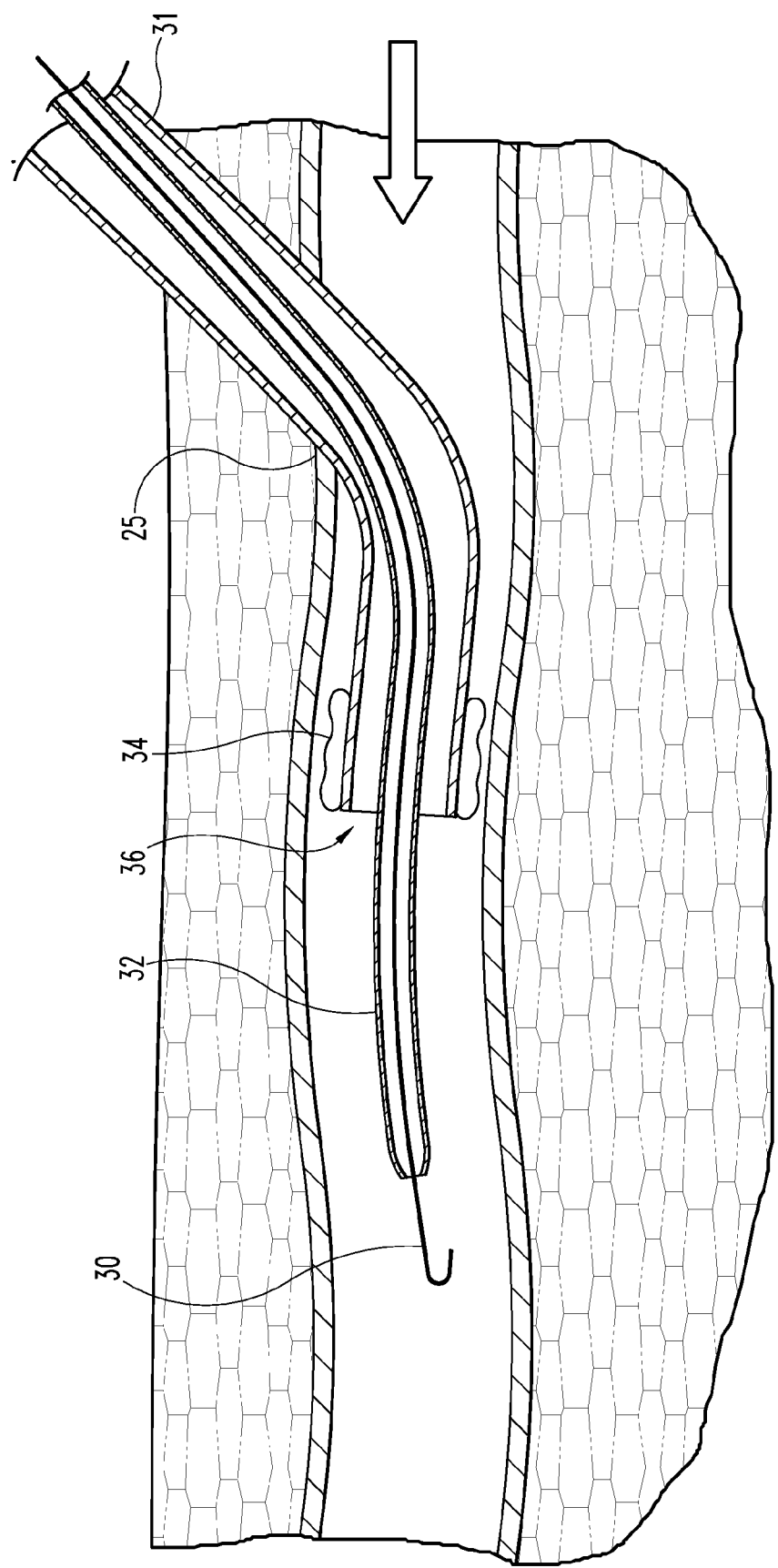
FIG. 2 shows a deployment embodiment in a venous vessel.

Turning more specifically now to FIG. 2, shown is an enlarged view of a bodily vessel. This vessel could, for example, represent a region of the GSV occurring generally between points 25 and 26 of FIG. 1. In an illustrative deployment procedure, percutaneous access to the GSV 21 can be achieved at point 25 using the Seldinger or any other suitable technique. For instance, an access needle (not shown) can be passed through the skin to access the GSV 21, and a J wire guide 30 or other suitable elongate guiding member can be passed through the access needle and into the vessel. In conjunction with or as part of an inventive method, wire guide 30 can be used for any number of conventional procedures including catheterization and imaging procedures to locate the sapheno-femoral junction 23 or other dilation procedures to open or otherwise straighten the GSV 21. After any such procedures are performed, the wire guide 30 can be removed or can be used to assist in the delivery of devices and materials within the GSV as described herein.

Specifically, referring still to the illustrative embodiment shown in FIG. 2, a deployment sheath 31 can be placed at a suitable location in the GSV 21 using a flexible guide catheter 32, or, alternatively, a suitable dilator or dilator tip mounted on the guide catheter. In placing or inserting the sheath 31 in the GSV, the guide catheter 32 can be first received over the wire guide 30, then pushed into the GSV 21, where it follows along the wire guide 30 to a location within the GSV 21. Next, the sheath 31 can be received over the guide catheter 32, pushed into the GSV 21, and follow the guide catheter 32 to a suitable location in the vessel. Alternatively, the sheath 31 and guide catheter 32 can be placed within the GSV 21, with the guide catheter 32 leading the sheath 31, and both can be pushed along the wire guide 30 until the sheath 31 is in a suitable location. Still alternatively, a steerable catheter can be used in conjunction with a sheath, thereby negating the need for a wire guide. Accordingly, inventive products and methods can be adapted to utilize any number of sheaths, catheters, wires and/or other endoluminally advanceable devices.

Endoluminally advancable devices useful in the invention (e.g., guidewires, catheters, endoscopes, etc.) can be shaped and configured in a variety of manners. A device might be constructed to traverse a body passageway without buckling or kinking or causing unacceptable damage to soft tissues defining the passageway. In some forms, the distal end of a device, or a portion thereof, will be particularly configured to avoid substantially cutting or tearing surrounding soft tissues or otherwise enhance its travel through body passageways. For example, a device distal end can include a tapered portion and/or have a dome-shaped or otherwise rounded tip. Selected portions of a device (e.g., the distal end), might be rigid, malleable, semi-flexible, or flexible. In certain embodiments, an endoluminally advancable device is particularly adapted for moving through and into body passages that angulate sharply or curve abruptly. In some of these embodiments, the device is configured to be directable or steerable through the passageway, and therefore exhibits desirable characteristics, e.g., sufficient stiffness, to allow an operator to apply an adequate degree of ante-grade force to the device to allow it to traverse a passageway in a desirable manner. In some forms, a device will be somewhat rigid in terms of column strength, yet will be equipped with one or more reliefs, indentations, thinner portions, or other similar adaptations along the device to provide some lateral flexibility to the device. Additionally or alternatively, a device may incorporate a mechanism of some sort that enables an operator to steer or otherwise navigate the device through a tortuous body passageway. These and other adaptations for facilitating advancement of a device through a body passageway will be recognized by those skilled in the art, and therefore, are encompassed by the present invention. In some aspects, components for visualizing and/or irrigating a body passageway can be received within an endoluminally-advancable device lumen as discussed herein.

Sheaths, dilators, endoluminal deployment devices, such as pushers, wire guides and needles, when used in the invention, can all be conventional marketed products or modifications thereof. For example, sheaths can be formed from PTFE (e.g. Teflon) or polyamide (e.g. Nylon) material, or a combination of materials such as an assembly including an inner layer of PTFE, a flat wire coil over the PTFE for kink resistance, and a polyamide (Nylon) outer layer to provide integrity to the overall structure and a smooth surface (e.g. as in the Flexor sheath, Cook, Inc.). Dilators and pushers can be made from conventional dilator/catheter/pusher type materials such as polyethylene, polyamide, polyurethane or vinyl, stainless steel, or any combination of these materials. Fittings provided for sheath/dilator assemblies can be conventional elements such as luer locks, and the dilator can have a fitting allowing it to be locked to the sheath during insertion and manipulation. Catheters can be made from conventional materials such as polyethylene, polyamide, PTFE, polyurethane, and other materials.

In some aspects of the present invention, it will be desirable to temporarily occlude a vessel region during a deployment procedure. In this regard, an endoluminal device might incorporate a balloon cuff or other outwardly (e.g., radially) displaceable component that can be used to fully or partially occlude the vessel around the endoluminal device at a particular vessel location. Various balloon and non-balloon devices for causing temporary occlusion are known to those skilled in the art, and these can be adapted for use in the present invention. Continuing with FIG. 2, this particular embodiment incorporates an inflation system that includes an expandable balloon cuff 34 positioned about the distal end of deployment sheath 31. Shown in an unexpanded or relatively lower-profile delivery configuration in FIG. 2, an expandable cuff of this sort can be placed at any suitable location along the deployment sheath, for example, at a location near the distal end but not interfering with devices entering or exiting the distal end opening 36 of the sheath. In accordance with certain aspects of the invention, following expansion of cuff 34, guide catheter 32 and wire guide 30 will be removed from the GSV 21, although these devices may be removed at any point during a procedure.

Figure 3:
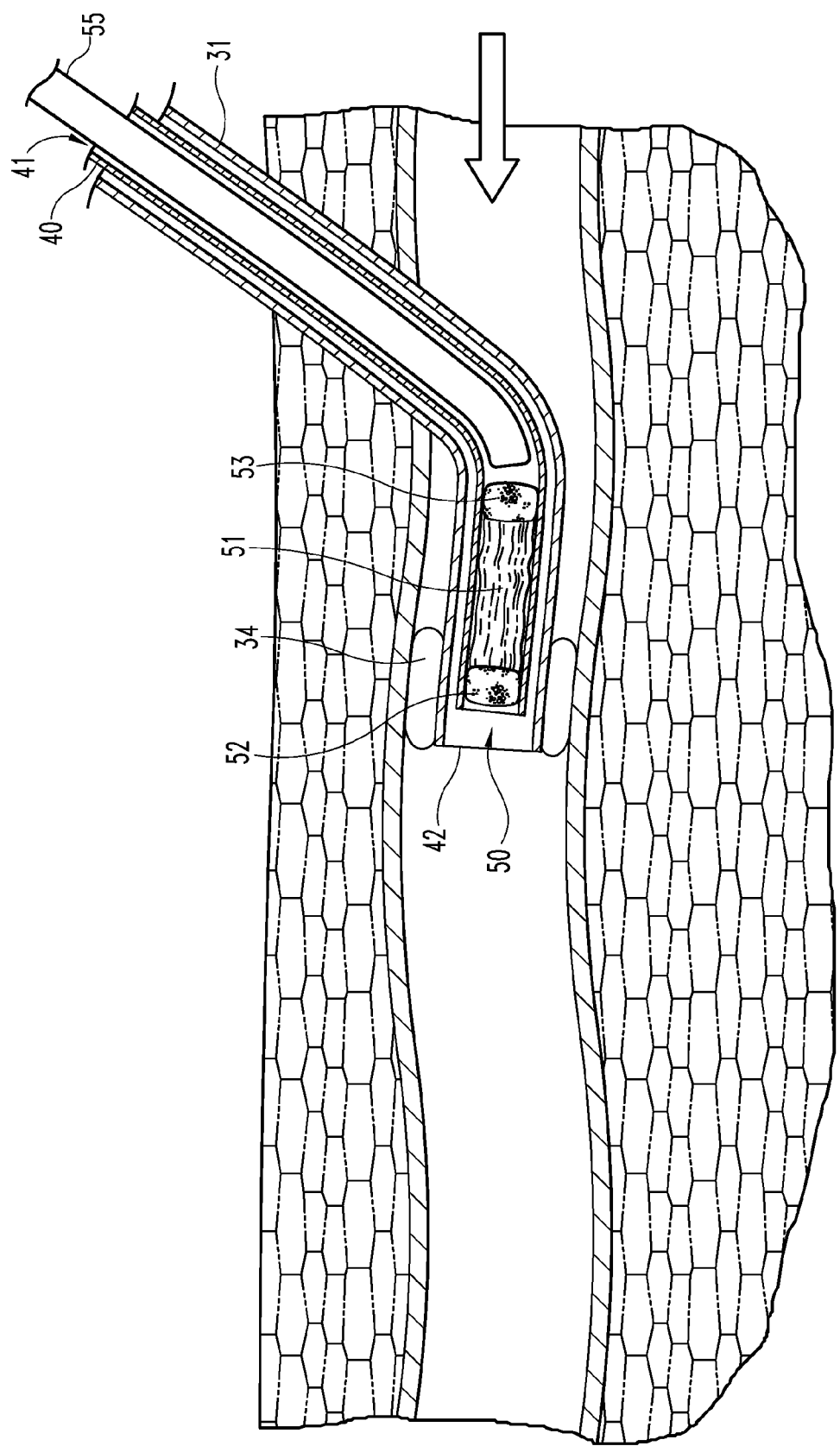
FIG. 3 is a partial view of an inventive medical product in a bodily vessel.

Accordingly, guide catheter 32 and wire guide 30 can be removed to leave sheath 31 in the vessel with an empty lumen for receiving other devices and/or materials. Illustrative sheaths will generally have an inner diameter (I.D.) ranging from about 4 French up to about 40 French. Referring now to FIG. 3, shown is deployment sheath 31 with balloon cuff 34 in an expanded condition which is effective to occlude the vessel around the sheath near its distal end. In an illustrative method, a flexible delivery catheter 40 is inserted into sheath 31 and advanced therethrough toward the distal, open end 36 of the sheath. Optionally, wire guide 30 can be left in the sheath, and other components such as delivery catheter 40 can be threaded over the wire and advanced to a desired location.

Continuing with FIG. 3, delivery catheter 40 has a lumen 41 that communicates with a distal opening 42. A vascular implant 50 is removably positioned in the catheter lumen, and is deployable therefrom through the distal opening 42 for placement in the bodily vessel. In this specific illustrative embodiment, implant 50 includes a hollow tubular segment 51. Tubular segment 51 exhibits a flexibility and thus can be folded and/or rolled over itself one or more times for placement in the catheter lumen. Implant 50 also includes a first expandable member 52 and a second expandable member 53 which are bonded, coupled or otherwise attached to opposite ends of segment 51. In alternate embodiments, an implant similar to implant 50 can be provided, except lacking expandable member 52, or lacking expandable member 53, thus providing one expandable member connected to segment 51; in these embodiments, the one expandable member (51 or 53) can be deployed "downstream" in blood flow relative to the position of segment 51 when deployed, such that flowing blood first contacts segment 51 and then member 51 or 53 (e.g. in some modes deploying member 51 or 53 closer to the heart than segment 51 in a venous deployment of the vascular implant). These types of expandable members can occupy any suitable volumetric shape, form, size, and material, and are shown compressed within the catheter lumen in FIG. 3. In one preferred embodiment, the expandable members are formed with a compressible material such as an extracellular matrix (ECM) sponge form material, although such components can be formed with a variety of sponge and non-sponge materials and devices. A pusher 55 is received in the catheter lumen, and is translatable through the lumen for urging the implant from the catheter.

Figure 4:
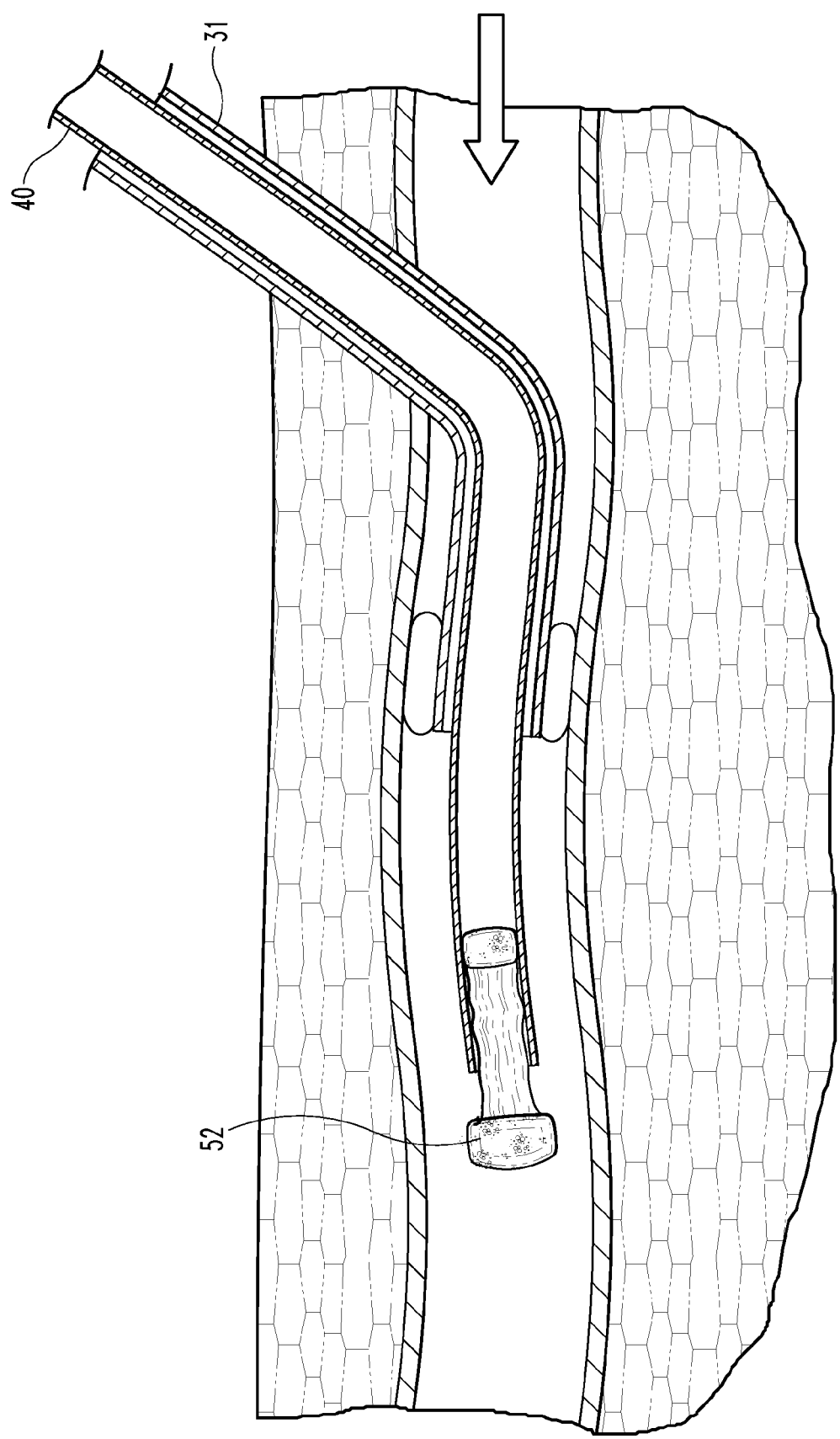
FIG. 4 shows a further illustrative use of the product of FIG. 3.

Turning now to FIG. 4, a further illustrative deployment step includes advancing delivery catheter 40 until it exits sheath 31 through its distal end. When the catheter is desirably positioned in the vessel, first expandable member 52 can be deployed from the catheter causing it to expand within the vessel. This sort of deployment can be achieved by holding the catheter in place in the vessel and forcing the expandable member out of the catheter by moving pusher 55 distally, by holding pusher 55 to maintain the expandable member steady and pulling back on the catheter, or a combination of the two. Expansion of the member can be facilitated by the presence of fluid in the vessel, e.g. patient blood, injected saline, etc., contacting the member either before, during, or after its deployment. When a pusher is used to force the implant out of the catheter lumen, it can make contact with any part of the implant to do so. With some designs, applying force to the second expandable member 53 will be sufficient to expel the implant from the catheter lumen. In some forms, a pushing device will extend through or around the second expandable member and through tubular segment 51 to apply force to the first expandable member 52, for example, by passing through an opening or other passageway in the second expandable member.

In this regard, occluding members that are pushable or guidable through a device lumen or a portion of a bodily vessel, e.g., implants comprising expandable foam pieces, layered constructs, etc. as discussed herein, will be utilized in certain forms of the present invention to achieve a desirable deployment. In some forms, occluding members can include an elongate foam or sponge cylinder or other member in a dried, compressed state, wherein the cylinder or other elongate member has sufficient column strength to be advanced on its own through a passageway by the application of force to the trailing end region of the member. In certain embodiments, the compressed material is effective to expand when wetted with water or other fluids, e.g. blood or other bodily fluids. Alternative such members can include a sheet material that is processed to itself such that it provides sufficient stiffness to the material to be advancable through a vein or other bodily vessel, or a material that incorporates certain rigid or semi-rigid materials or objects that enhance the stiffness of the occlusive material to make the material guidable through a bodily lumen, if desired.

Suitable such implants can include occluding components that exhibit a column strength of at least about 200 kPA, for instance between about 200 kPA and about 12,000 kPA or more. In additional embodiments, an occluding member has a column strength of at least about 700 kPA, for example within the range of from about 700 kPA to about 11,000 kPA. Still additional devices can have column strengths from about 1,000 kPA to about 10,000 kPA, or from about 1,000 kPA to about 3,000 kPA. Such column strength values can be measured using a conventional Instron compressive strength testing machine. A sample of occlusive material, 5 cm in length, can be secured between to two test fixtures such that 0.5 cm of material is held within in each fixture. This test assembly results in a span of 4 cm of occlusive material between each fixture face. Thereafter, the fixtured sample can be placed in the Instron testing machine and compressed at a rate of 30 mm/min until the sample buckles. The force recorded at the point of buckling is the column strength or pushability number of the occlusive material.

In certain work performed to date, three segments of a dry small intestine submucosa foam material, each having a pre-compressed diameter of 16 mm and a length of 5 cm, were compressed down to a diameter of 4 mm using a radial compression device. Thereafter the column strength of each sample was individually determined using an Instron compressive strength testing machine. Each test was performed by securing 0.5 cm of each end of each sample within a test fixture such that a span of 4 cm of compressed foam material extended between the faces of the fixtures. The fixed sample was then compressed by the Instron machine at a rate of 30 mm/min and the compressive force was recorded. The compressive force at the point each test sample buckled was recorded as the column strength or pushability number for each sample. The column strengths for the foam samples were determined to be 1488.5 kPA, 1849.6 kPA, and 1628.8 kPA, respectively.

Figure 5:
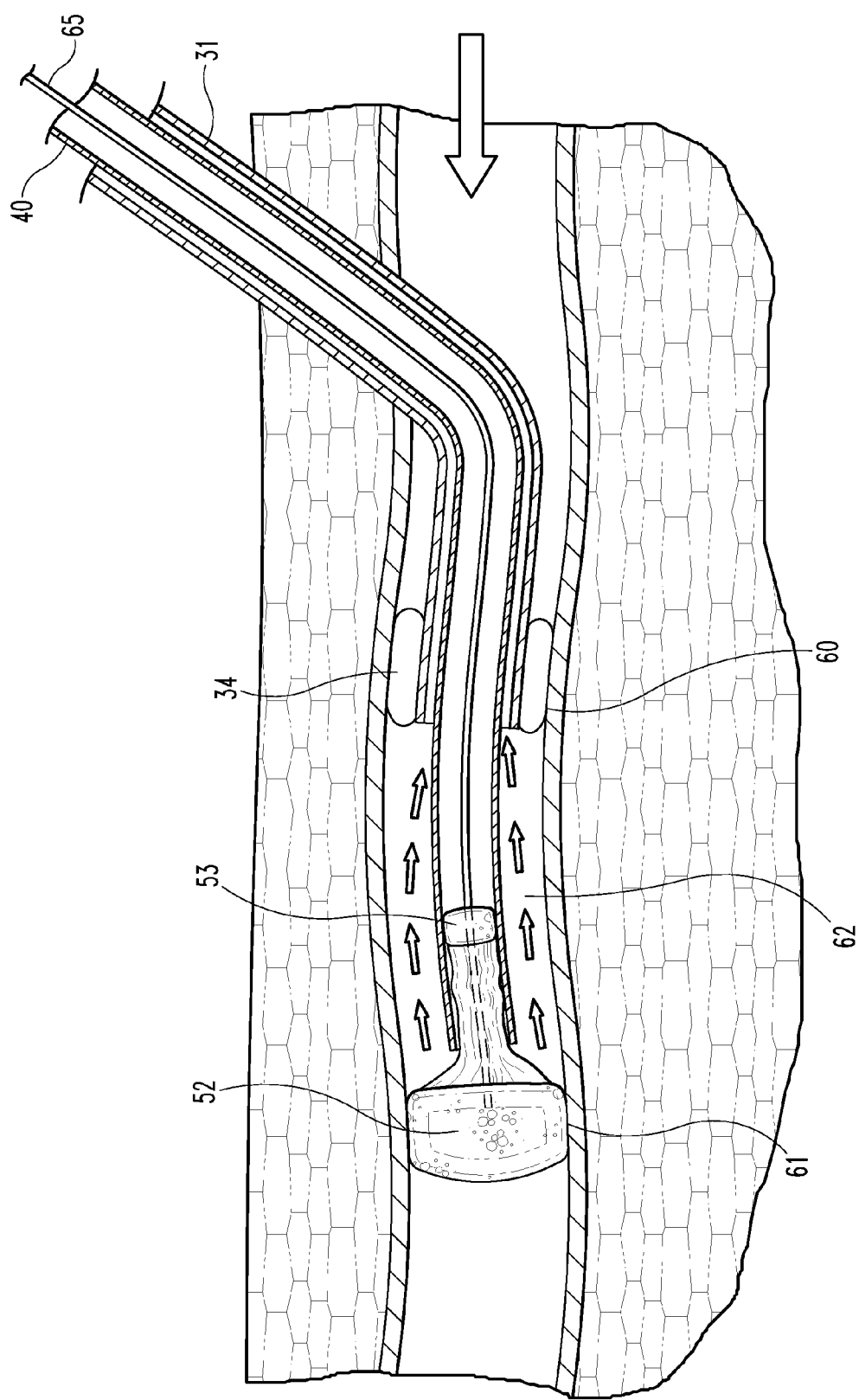
FIG. 5 depicts still a further use and additional components that may be used in the product of FIG. 3.

Continuing with the illustrated embodiment, first expandable member 52 will continue to expand following deployment from the catheter until it sufficiently contacts inner surfaces of the vessel to occlude or substantially occlude the vessel as shown in FIG. 5. With certain designs, this expansion and contact will be sufficient to maintain the member 52 at a particular location in the vessel following deployment, although some inventive implants will incorporate one or more anchoring or securement adaptations (not shown) so as to mitigate undesirable migration of the device within the vessel. In some instances, parts of a device will embed themselves in the vessel wall upon deployment and/or any subsequent repositioning of the device in the vessel. Any number of anchoring adaptations, barbs, hooks, ribs, protuberances, and/or other suitable surface modifications can be incorporated into an inventive device to anchor and/or roughen, condition, or otherwise de-epithelialize at least a portion of the vessel wall during and/or after deployment of the device within the vessel. The conditioning of the vessel wall tissue can serve to initiate a localized healing response in patient tissue that can be advantageous in enhancing the ingrowth of patient tissue into an inventive device, such as a device that is comprised of a tissue ingrowth receptive material.

As shown in FIG. 5, balloon cuff 34 is effective to occlude the vessel around sheath 31 at a first vessel location 60, and expandable member 52 is effective to occlude the vessel at a second vessel location 61. With this sort of arrangement, an intermediate vessel segment or working segment 62 is formed generally between first location 60 and second location 61. Because the distal, open end 36 of sheath 31 maintains fluid communication with working segment 62, it is possible to pass fluids into and out of the working segment through sheath 31. When the vessel being treated is a blood vessel, working segment 62 will generally contain an amount of blood. In some instances, it may be desirable to evacuate all or part of this blood from the vessel segment.

In some embodiments, components for irrigating a body passageway can be received within an endoluminally advancable device lumen. Illustratively, such components, as well as other desirable instruments and/or materials, can be passed into the proximal end of the device lumen (or alternatively, can be passed into one or more openings in a sidewall of the device), and through at least a portion of the device lumen. For example, in certain aspects, a device of the invention includes one or more ports in a sidewall thereof, wherein each port can be associated with a corresponding channel that extends from the port toward the distal end of the device. In some forms, one or more port and channel combinations are each configured to receive one or more instruments and/or materials therethrough. For example, a port can be configured to receive one or more optical fibers for visualization and/or illumination of a body passageway and surrounding soft tissues, for example, fiber-optic bundles including a plurality of glass fibers comprised of silicone, silicone dioxide, and/or a suitable equivalent.

When irrigation fluids are used in conjunction with the present invention, such fluids can be provided from an external bag of fluid that is connected to a device port of the irrigation channel by means of flexible tubing. If necessary, the fluid can be infused under pressure using a pressure bag applied to the fluid source, to increase the pressure under which the fluid is infused. Suitable device ports can further be configured to receive guide-wires, drains, solutions such as sealants or sclerosants, high intensity light sources, a lever system to steer the device (e.g., wherein the device and/or its distal tip is directable in one, two, or three planes), and/or any other suitable instruments and/or materials. In some forms, a device port is configured to receive an optical viewing and lens system that may be attached to a video camera, a video monitor, and a video recorder for viewing at the distal end of the device.

Accordingly, the illustrated embodiment can incorporate an irrigation system and sump system to inject fluids into and evacuate fluids from working segment 62 through sheath opening 36. When utilized, irrigation and sump components can be shaped and configured in a variety of manners, and their positioning relative to the other device components can be adapted as desired to access the working segment. An irrigation device could, for example, extend through sheath 31 either internally or externally of delivery catheter 40 in the current embodiment. In some forms, an irrigation tube will extend through the delivery catheter and work in conjunction with the implant, e.g., passing into and/or through the implant, to deliver irrigation fluid to areas of the working segment occurring externally of the implant.

As shown in FIG. 5, an illustrative irrigation system includes an irrigation tube 65 that extends through delivery catheter 40, and also through second expandable member 53 and tubular segment 51 to reach the first expandable member. First expandable member 52 provides at least one passage through which irrigation and other fluids can pass.

Figure 6A:
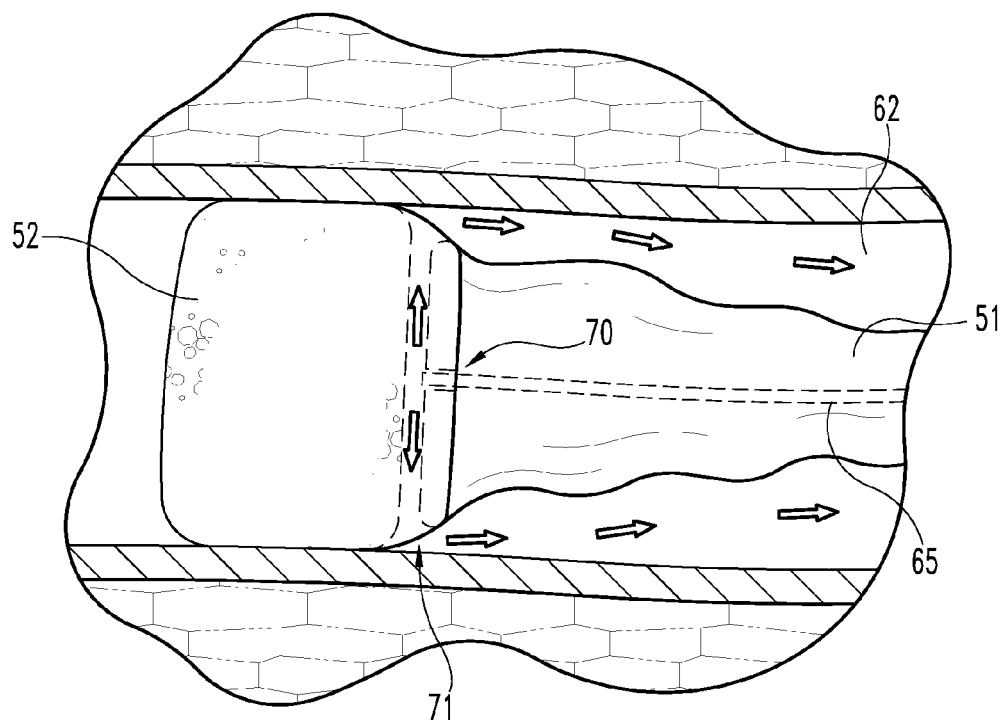
FIG. 6A is a partial view of an irrigation system embodiment.
Figure 6B:
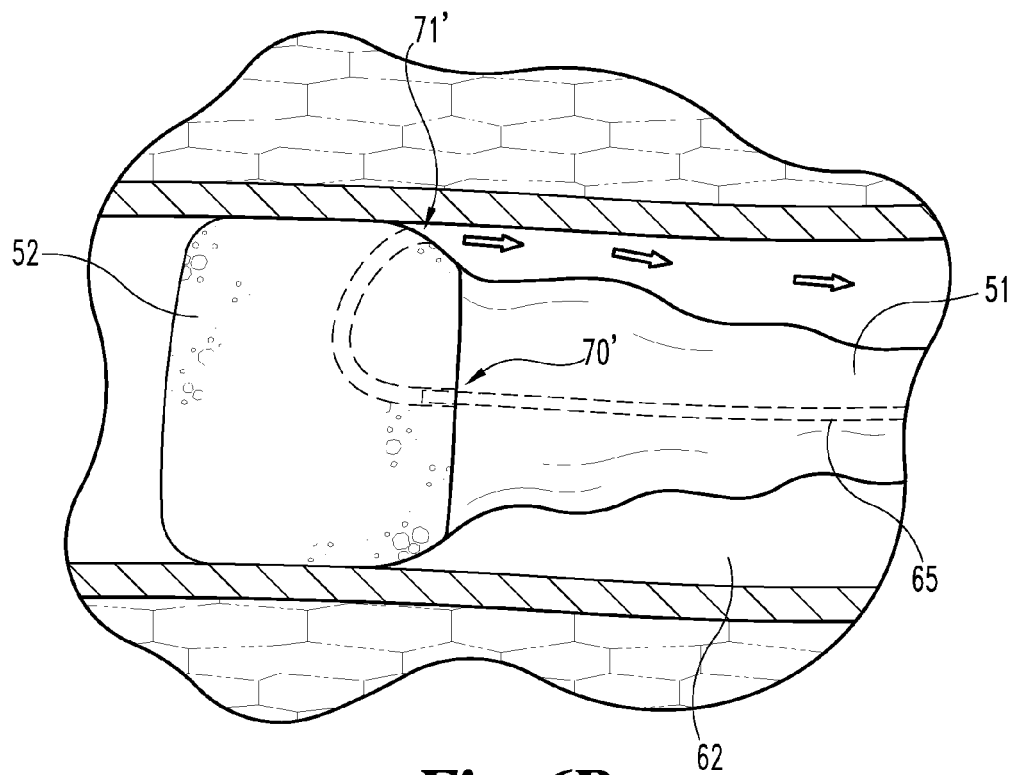
FIG. 6B is a partial view of an irrigation arrangement according to another embodiment of the invention.

Irrigation tube 65 communicates with one or more of these passages, and will extend into and potentially through the passage(s) in some embodiments. FIGS. 6A and 6B show alternative embodiments where the irrigation tube and the first expandable member are configured to work together to direct irrigation fluid through the implant and back into areas of the working segment 62. In FIG. 6A, a channel system includes an inlet opening 70 and two outlet openings 71. The distal end of irrigation tube 65 extends into opening 70 so that irrigation fluid can flow through the tube and channel system and back into regions of the working segment (externally of tubular segment 51 as indicated by the arrows). In FIG. 6B, a channel has an inlet opening 70' and a single outlet opening 71'.

Referring back to FIG. 5, as irrigation fluid exits the distal part of the implant, it flows into working segment 62 and mixes with blood and/or other bodily fluids in the vessel. With an appropriate evacuation system, this mixture will flow alongside the delivery catheter 40 (which still houses portions of the implant including the second expandable member 53) and into the distal, open end 36 of the outer sheath 31 to exit the body. The flow of irrigation fluid can be continued until essentially all of the blood has been removed from the working channel 62. Thereafter, the irrigation tube 65 can be withdrawn and removed from the vessel. Having irrigation fluid enter the working segment in a distal region of the segment, although not necessary to broader aspects of the invention, can lead to quicker and otherwise more effective flush of the vessel segment.

Figure 7:
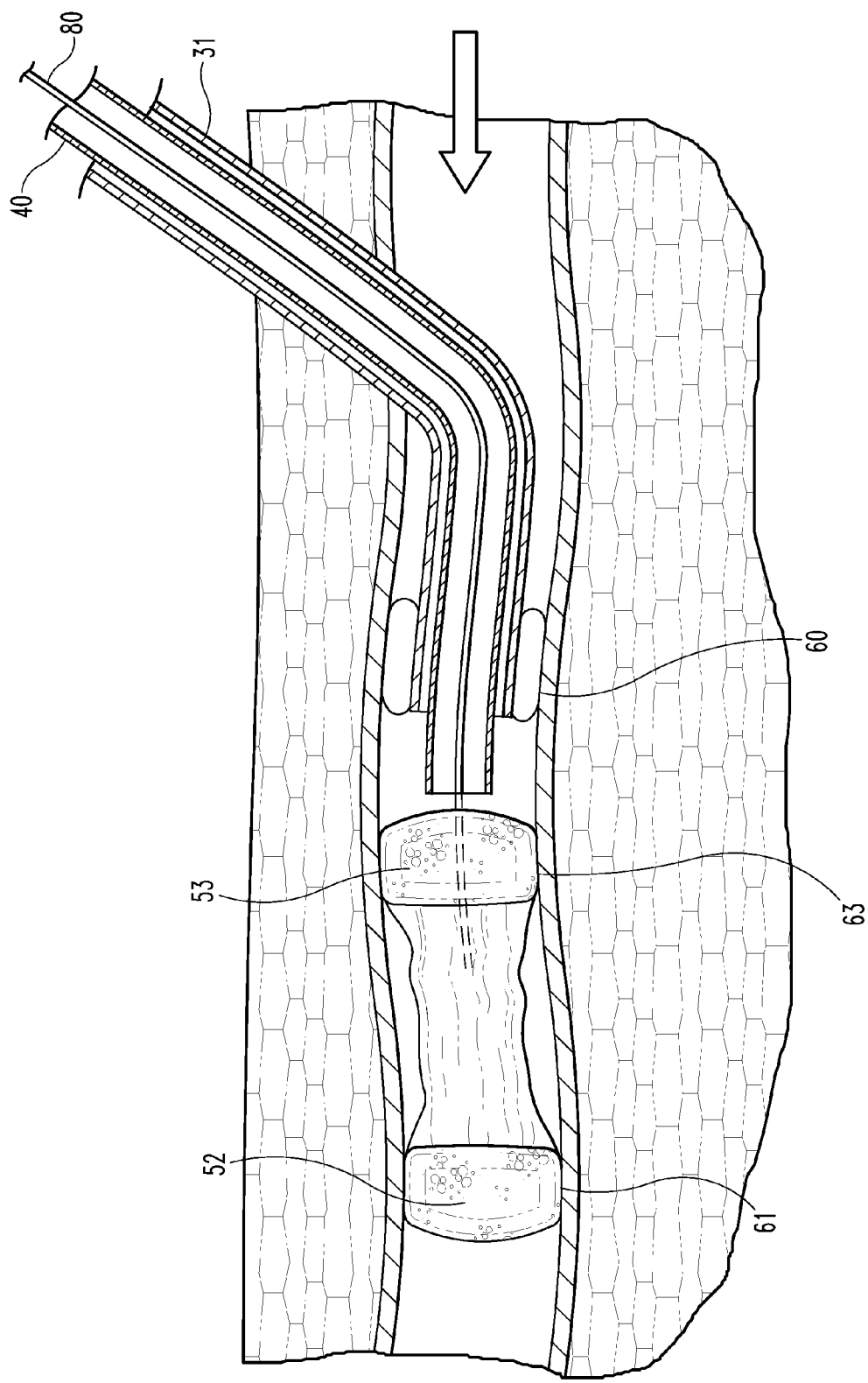
FIG. 7 depicts still a further use and additional components that may be used in the product of FIG. 3.

Turning now FIG. 7, a further illustrative deployment step includes deploying the second expandable member 53 (when present) from the delivery catheter so that it expands to occlude or substantially occlude the vessel at a third vessel location 63 located between first location 60 and second location 61. This particular illustrative implant can be adapted so that it retains enough compressibility following deployment to allow the surrounding vessel to squeeze the implant nearly flat without significantly affecting its ability to occlude the vessel. In some instances, deployment of the second expandable member will essentially conclude the procedure, and the sheath 31 and any or delivery components present will be removed from the vessel. In some other instances, one or more additional steps will be carried out following deployment of the second expandable member from the catheter. Further steps might include deploying additional implants and/or placing a substance in and/or around the implant(s), for example, a drug, sclerosant, biotropic material and/or other suitable material. When multiple implants are deployed, achieving occlusion at the first implant deployment can reduce concerns of pulmonary thromboembolism or particulates traversing an inadvertent PFO that might be associated, for example, with the deployment of subsequent implants.

In some inventive embodiments, one or more agents or other substances (see below) can be conjunctively or cooperatively emplaced within a patient with one or more occlusive implants as are discussed herein. Cooperative emplacement can include the contact of patient tissue with agents before, after, and/or while the occlusive device is implanted in the patient. Such tissue contact of agents can occur in those areas that will become or are in contact with one or more occlusive devices and/or are adjacent to or near the implant or prospective implant location. For example, the agents can be delivered into the patient through a cannulated lumen, such as before an occlusive device (e.g., device 50) is implanted, or can be injected into a patient through a needle and syringe, such as after an occlusive device is implanted. In additional embodiments, the agents can be contained within or on the occlusive device, such as by being applied to an occlusive construct by a physician before implantation occurs, and/or by being doped, bonded, or otherwise contained within a dry occlusive construct, such as can be achieved by soaking a construct in one or more agents and thereafter drying and packaging the construct.

It might be desirable, with certain embodiments, that a portion of an implant such as the interior region of tubular segment 51 be filled with a fill material. A fill material may already reside in a region of an implant prior to deployment and/or a fill material can be located in an implant after the implant is deployed in a vessel. Turning now to a discussion of fill materials useful in some aspects of the invention, a vessel segment and/or an occluding body can be filled with any material conducive to achieving chronic occlusion of a vascular vessel of interest. In this regard, the fill material may be a solid, liquid, gel, foam or gas, such as blood, polymer, contrast medium, a remodelable or bioabsorbable material, saline, a non-bioabsorbable material, collagen rods or particulates, a collagenous or gelatinous foam, air, chitosan, gelatin, oxidized regenerated cellulose, calcium alginate, alginate, thrombin-fibrin enhanced materials, fibrin glues, or any suitable combination thereof.

In one embodiment, the fill material can comprise a comminuted, fluidized, and/or gelatinous remodelable material. For example, a remodelable gel can be formed from fluidized compositions, as illustrated in U.S. Pat. Nos. 5,275,826, 5,516,533, 6,206,931, and/or International Publication No. WO2005020847 (Cook Biotech Incorporated) published Mar. 10, 2005, which are each hereby incorporated by reference in their entirety. In this regard, solutions or suspensions of ECM can be prepared by comminuting and/or digesting ECM with a protease (e.g. trypsin or pepsin), for a period of time sufficient to solubilize the ECM and form substantially a homogenous solution. The ECM starting material is desirably comminuted by tearing, cutting, grinding, shearing or the like. Grinding the ECM in a frozen or freeze-dried state is advantageous, although good results can be obtained as well by subjecting a suspension of pieces of the submucosa to treatment in a high speed blender and dewatering, if necessary, by centrifuging and decanting excess waste. The comminuted ECM can be dried, for example freeze dried, to form a powder. Thereafter, if desired, the powder can be hydrated, that is, combined with water or buffered saline and optionally other pharmaceutically acceptable excipients, to form a fluid composition, e.g. having a viscosity of about 2 to about 300,000 cps at 25° C. The higher viscosity compositions can have a gel or paste consistency. This gelatinous composition can be used as fill material in certain embodiments of the invention.

Additionally, such gelatinous or flowable materials can include solubilized and/or particulate ECM components, and in preferred forms include ECM gels having suspended therein ECM particles, for example having an average particle size of about 50 microns to about 500 microns, more preferably about 100 microns to about 400 microns. The ECM particulate can be added in any suitable amount relative to the solubilized ECM components, with preferred ECM particulate to ECM solubilized component weight ratios (based on dry solids) being about 0.1:1 to about 200:1, more preferably in the range of 1:1 to about 100:1. The inclusion of such ECM particulates in the ultimate gel can serve to provide additional material that can function to provide bioactivity to the gel (e.g. itself including FGF-2 and/or other growth factors or bioactive substances as discussed herein) and/or serve as scaffolding material for tissue ingrowth.

Alternatively, the fill material can comprise a suitable solidifying polymer, such as HEMA. Upon addition of a catalyst to HEMA at a certain temperature, HEMA will gradually change from a liquid form to either a gelatinous or solid form over approximately twenty minutes. This change in form is desirable in a fill material because the material can easily flow into the occlusion device, eliminating void space between the device and the vessel wall, and then solidify, thereby enhancing the occlusion ability of the device. For more information on HEMA and other fill materials useful in the present invention, reference can be made, for example, to U.S. Pat. Nos. 4,819,637, 5,222,970, 5,304,123, 5,411,475, and/or 5,830,228, each of which is hereby incorporated herein in its entirety.

Additionally, the fill material, including, e.g. remodelable ECM fill materials, can include one or more radiopaque and/or echogenic markers or a radiopaque coating or impregnation to assist in visualization of the material during a non-invasive procedure. For example, radiopaque substances containing tantalum, barium, iodine, or bismuth, e.g. in powder form, can be coated upon or incorporated within a fill material, such that, for example, the location of the fill material within a patient's body can be detected.

In certain embodiments, a fill material will include a substance that is capable of bringing about or inducing constriction, spasm, or closure in a bodily vessel of a patient and/or causing the de-epithelialization or inflammation (either dilative or constrictive), and/or otherwise initiating a healing response in patient tissue, such as a wall segment of a venous vessel. Such agents can include any suitable vasoconstrictive agent, sclerosive agent, thrombogenic agent, inflammatory agent, hypercoagulable agent, or any suitable combination of one or more of any of the above or other suitable agents. For example, suitable vasoconstrictive agents can include any suitable alpha adrenergic direct or indirect agonist, such as norepinephrine, epinephrine, phenylephrine, and/or cocaine, or lidocaine, hypertonic saline, or any suitable combination thereof. Illustrative sclerosive agents can include, for example, polidocanol, sodium tetradecyl sulfate, e.g. SOTRADECOL®, morrhuate sodium, ethanolamine oleate, tetradecyl sulfate, tetracycline, glycerin, hypertonic glucose, talc, acetic acid, alcohol, bleomycin, picibanil, ethibloc, deoxycycline, and/or any suitable microfoam that contains a sclerosive agent, such as VARISOLVE®, manufactured by Provensis, Ltd. of London, England, or any other suitable agent as disclosed in U.S. Pat. Nos. 5,676,962 and/or 6,572,873, for example. In some aspects, an anesthetic agent may be added to a sclerosant agent mixture or other fill material.

Figure 8:
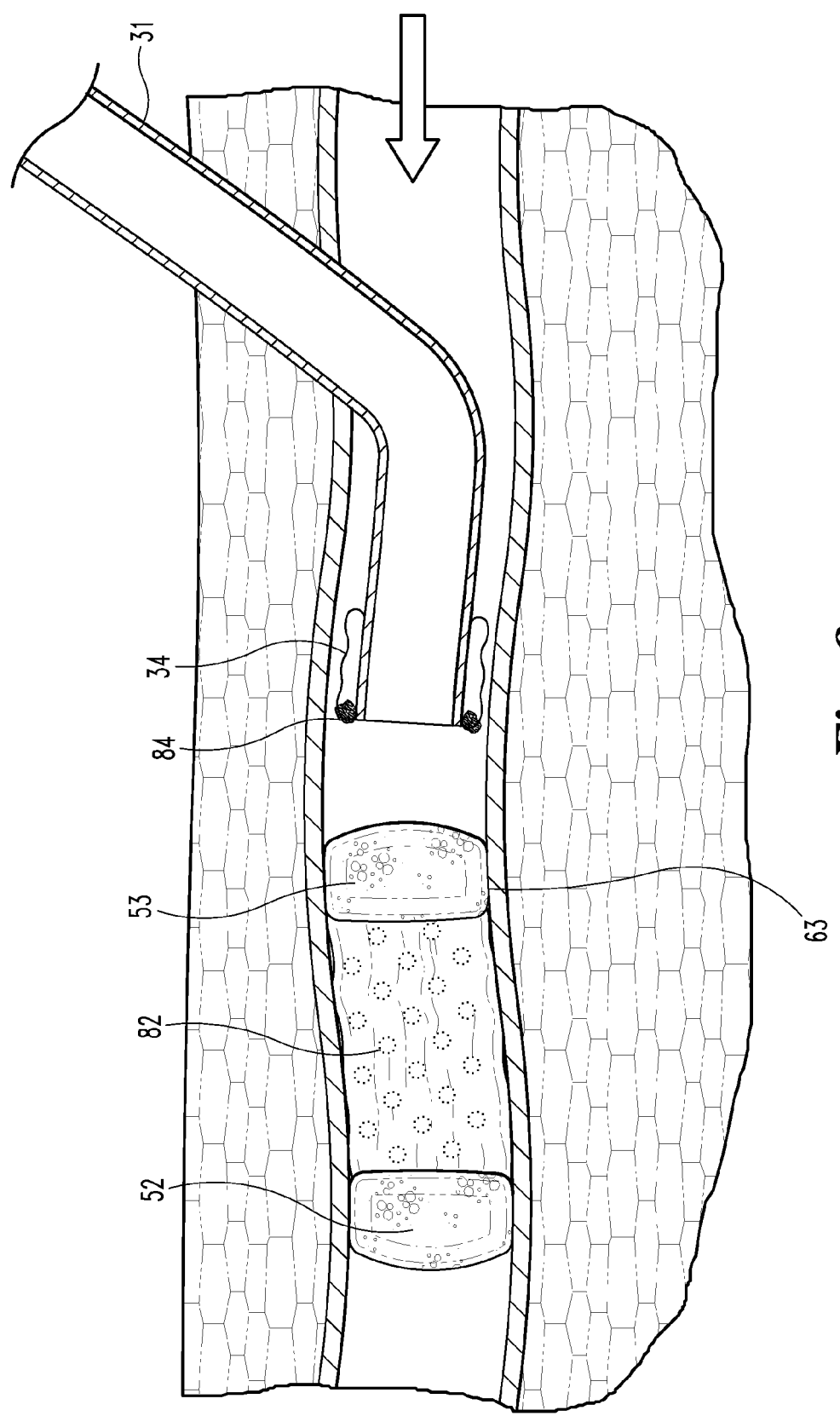
FIG. 8 shows an inventive implant deployed in a bodily vessel.

Referring still to FIG. 7, in this specific illustrative embodiment, an injection tube 80 is caused to extend into an interior region of tubular segment 51 for at least partially filling this region with a fill material such as a sclerosant. In some designs, the above-described irrigation system will be adapted to deliver fill material to the implant. Filling the flexible tube 51 with fill material will generally force the walls of the tube toward the walls of the vessel. FIG. 8 shows tube 51 after it has been filled with fill material so that tube 51 essentially lines the inside of the vessel and makes significant contact with the vessel walls. In this condition, the filled implant in turn substantially fills working segment 62 including any void space that might have previously existed between the implant and the vessel walls. Once the tubular segment is desirably filled, the injection tube can be withdrawn and removed from the body, and the balloon cuff 34 can be deflated in preparation for removing sheath 31 from the body or for repositioning the sheath to carry out one or more additional steps, e.g., deployment one or more additional implants.

Implant portions that are capable of receiving fill materials such as tubular segment 51 can be formed with one or more of a variety of materials, some of which will be synthetic and others non-synthetic. These types of implant portions can occupy any suitable volumetric shape, form, size, and material. In some aspects, a wall of material will be constructed to provide a fillable interior where the wall is made of a sheet or sheet-like material. In some preferred embodiments, a tubular or other wall segment will be formed with a collagen-containing material such as a reconstituted collagen sheet or a harvested ECM material layer. Additionally or alternatively, a wall segment or other implant body portion can include a synthetic polymeric material such as Dacron. Particular advantage will be provided by some products in which all or part of the implant is formed with a material that is receptive to tissue ingrowth.

Additionally, in some embodiments, an implant body portion such as tubular segment 51 will have one or more openings 82 or passages in a wall thereof (as shown in phantom in FIG. 8). With this sort of design, native and non-native substances can pass through the openings to enter and exit an implant interior, for example, where a fill material is present in a hollow connecting segment and is able to exit the segment through side wall openings. Depending on the types of fill materials utilized, particular advantages can be provided by having the fill material(s) pass through the openings and into contact with the surrounding vessel wall surfaces, for example, where a sclerosing agent contacts a vein wall causing the vein to spasm and constrict or otherwise tighten around the implant, or as otherwise discussed herein with regard to bioactive and other fill materials. Further, if substantial occlusions occur at second location 61 and third location 63, materials and substances located in working segment 62 will essentially be contained there, at least initially, and not allowed to migrate to other locations in the vessel anatomy. This type of arrangement might be particularly advantageous in situations where a substance proves to be beneficial at a treatment site but there are reasons to want to contain that substance in the general vicinity of the site, for example, where a sclerosant might unintentionally migrate and enter a perforator vein causing deep venous thrombosis.

It may be advantageous, in certain situations, to create a working segment as an environment to protect early clot development where blood components are present, and if an implant is receptive to tissue ingrowth, to protect early tissue formation occurring at the occlusion site. When all or part of an inventive device incorporates a tissue ingrowth receptive material, a sealed off or substantially sealed off working segment such as that shown in FIG. 8 can provide a more effective environment for the tissue ingrowth to take place. Upon deployment of such a device in accordance with certain aspects of the present invention, cells from the patient can infiltrate the material, leading to, for example, new tissue growth on, around, and/or within the device. In some embodiments, one or more device components will be comprised of a remodelable material, and its ability to remodel can be enhanced when placed in a protected working segment. In these embodiments, the remodelable components promote and/or facilitate the formation of new tissue, and are capable of being broken down and replaced by new tissue in such a way that the filling of a space by a deployed device is maintained throughout the remodeling process so as to eventually fill the space with new tissue.

Openings in an implant body can exhibit a variety of shapes and configurations. Openings can exhibit curvilinear and/or rectilinear features. Illustratively, shapes of openings include but are not limited to those that are essentially circular, oval, square, rectangular and diamond-shaped. When a wall or other component includes a plurality of openings, all of the openings may be of the same type, or alternatively, any one opening may be shaped and configured differently than any other opening. An opening can be a slit or a non-slit opening. Spacing between or among openings can vary across a construct. Openings can be arranged in a pattern of some sort, or an arrangement of openings can be fully or partially randomized in a material. Some embodiments will include rows or lines of openings, although other recognizable groupings of openings can be employed as well.

A component can have any suitable number of openings, and these openings may or may not be located across all parts of the component. With some implants, openings will occur exclusively or primarily in end portions of a body, although openings can additionally or alternatively occur in non-peripheral regions of a body. As well, an opening may or may not be pre-existing in a material. In instances where a fully or partially manufactured material is utilized, the material can be manufactured so as to have one or more openings. In some forms, a material will be provided, and one or more openings will then be formed in the material. Forming an opening in a material can be accomplished in a variety of ways including some that involve use of scissors, a punch, a knife or scalpel, a laser cutter or any other suitable instrumentation known for making an opening in a material.

In certain embodiments, it may be advantageous to process a sheet or other material, or any portion thereof, so that it exhibits a meshed structure. Illustratively, a meshed structure can have a plurality of slits therein to provide a mesh pattern, and the mesh pattern can be useful to provide deformability to the structure, and in some case, expandability. In this regard, in some meshed constructs, expansion or other deformation of the structure will widen the openings created by the slits of the mesh pattern, by lateral and/or vertical displacement of the edges of the slits relative to one another. Certain meshed devices of the invention will have a mesh pattern providing an expansion ratio of at least about 1.2:1 when the layer is completely hydrated, more preferably at least about 2:1, and most preferably at least about 3:1. Such highly deformable structures provide surprisingly beneficial properties to the graft product, particularly in the field of wound care.

A meshed pattern can be created using suitable meshing devices designed for processing skin autograft sections. Such devices can include a cylindrical drum cutter with a plurality of edges for providing the slit pattern of the mesh. A variety of such devices are known and can be used in the invention. For additional information as to meshers, reference may be made to U.S. Pat. Nos. 5,004,468, 6,063,094, 3,472,228, 3,358,688, and 3,640,279. These and other devices incorporating a meshing drum provide for a convenient, high-throughput method of preparing meshed material layers or graft devices of the invention. It will be understood, however, that the mesh pattern can be made by hand-cutting the material or by using appropriate cutting tools with multiple blades to cut the slits to provide the mesh pattern.

Additionally, sheath 31 includes an optional radiopaque component 84 about its distal end. As is known, the distal ends, or any desirable segment or portion, of the catheters, sheaths, dilators, wires or other components, such as occlusive devices, used in percutaneous procedures can include markers that can be X-ray, sonographically, or otherwise non-invasively visualized to identify their location during the procedure. Metallic bands of stainless steel, tantalum, platinum, gold, or other suitable materials, which include a dimple pattern, can serve the purpose for both ultrasound and X-ray identification. As well, distal and/or proximal ends and/or other locations on occluder devices may include markers for non-invasive imaging, including imageable materials such as those discussed above as well as substances that can be incorporated into occluding materials, e.g. radiopaque elements such as but not limited to a radiopaque coating, attached radiopaque object, or integrated radiopaque substance. Any suitable radiopaque substance, including but not limited to, tantalum such as tantalum powder, can be incorporated into a medical product of the invention. Other radiopaque materials comprise bismuth, iodine, and barium, as well as other suitable markers.

Figure 9:
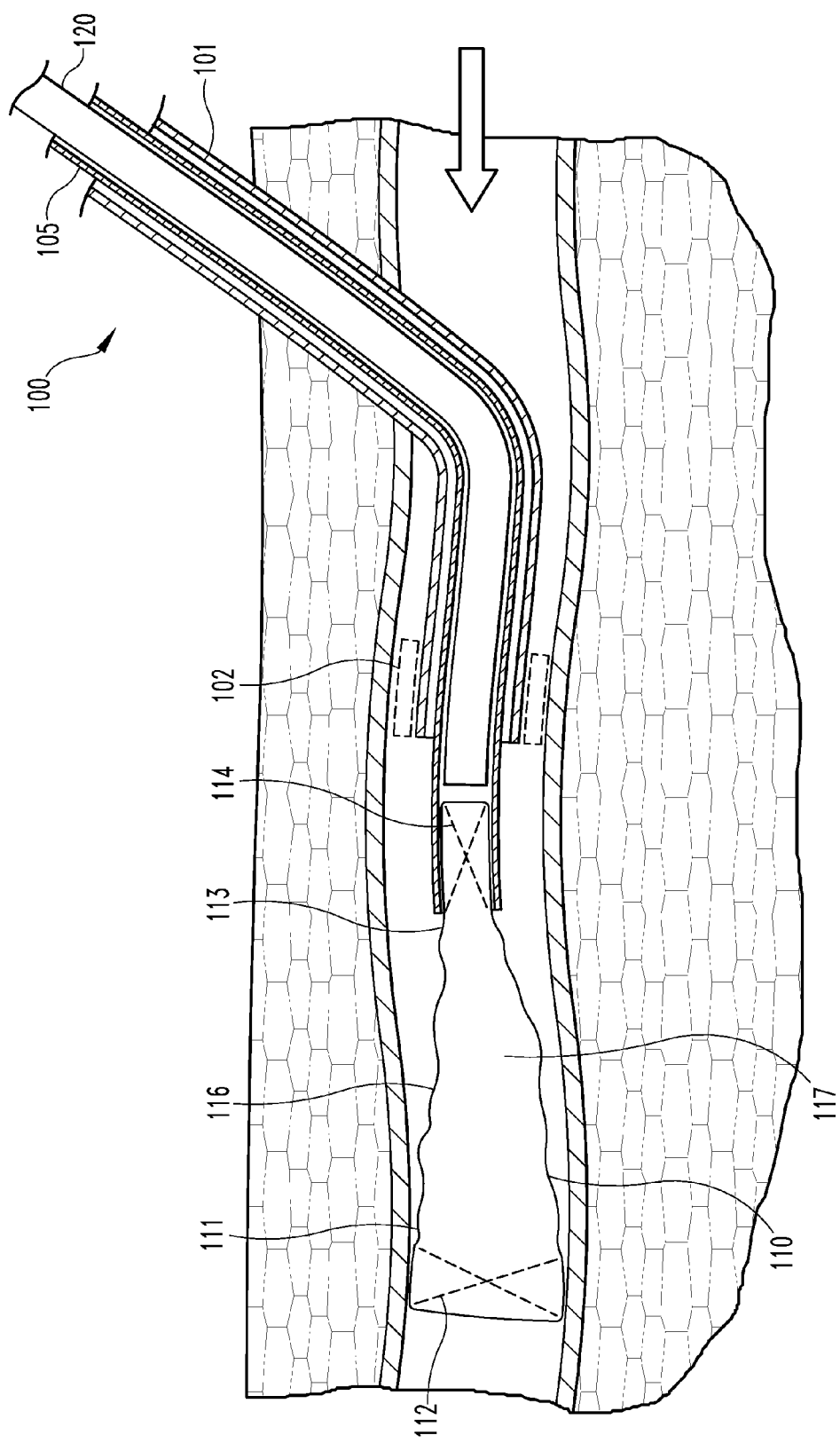
FIG. 9 is a partial view of another inventive medical product in a bodily vessel.

With reference now to FIG. 9, shown is a medical product 100 according to another embodiment of the present invention. Product 100 includes an outer sheath 101 having an optional flow stoppage component 102 positioned along a distal portion of the sheath. Component 102 may be or include an inflatable or non-inflatable device, and when activated is effective to make sufficient contact with the surrounding vessel wall to essentially stop flow past the sheath in the vicinity of the component. Product 100 also includes a flexible inner sheath 105 that is deliverable into the vascular vessel through outer sheath 101. Inner sheath 105 has a lumen capable of housing one or more vascular implants for deployment into the vessel.

FIG. 9 shows an illustrative implant 110 being deployed in a vessel. Implant 110 has a first end portion 111 that is comprised of a first expandable member 112, and a second end portion 113 that is comprised of a second expandable member 114. A wall of material 116 extends between the end portions, and by its construction provides a hollow or otherwise interior space 117 (hidden) into which one or more fill materials may be placed if desired. Each of the expandable members is compressible to fit inside the delivery sheath lumen, and expandable upon removal from the lumen. In some forms, at least one of the expandable members will incorporate a frame or frame-like component to provide some or all of the expansion, although expandable members lacking frames as discussed herein can be utilized in this embodiment as well. Illustratively, a frame component can be embedded in or otherwise associated with a sponge, sheet and/or other occlusive material to promote and/or facilitate the stoppage of slow past an implant portion. In one embodiment, one or more self-expandable frames are positioned about a tubular segment, e.g., in and/or around a tube having open or closed end(s).

In an illustrative method, the inner sheath 105 is delivered to the vascular vessel and advanced beyond the distal end of outer sheath 101 to a desirable location in the vessel. This step can be performed with or without the stoppage of flow around outer sheath 101 using component 102. Thereafter, first expandable member 112 is forced from the delivery sheath lumen so that it expands to position the first end portion 111 in the vessel to block flow through the vessel, for example, using a pusher 120. With or without relocating inner sheath 105 in the vessel, second expandable member 114 can then be forced from the delivery sheath lumen so that it expands to position the second end portion 113 in the vessel to block flow through the vessel. With this type of design, there are a variety of ways to deploy the different implant components from inner sheath 105. In some aspects, following deployment of the first expandable member, the delivery sheath 105 will be retracted a distance to draw the material 116 out of the sheath lumen as shown in FIG. 9. Thereafter, the second expandable member can be forced from the catheter lumen with the aid of pusher 120. In certain forms, first end portion 111 will be sufficiently anchored in the vessel following deployment, e.g. through expansion of member 112 and/or other anchoring techniques discussed herein, so that retracting the delivery catheter will be effective to pull the second expandable member from the catheter lumen. As with other inventive embodiments, optional irrigation and/or sump components can be incorporated into this system for use during any of the deployment steps. Thereafter, the pusher, sheaths and any other deployment pieces present can be withdrawn and removed from the body, leaving the implant 110 behind in the vessel.

Turning now to a discussion of frame and frame-like elements that can be incorporated into inventive implants such as implant 50 and implant 110, these various elements can include single- and multiple-part devices. In some forms, a frame member will include a filament or wire body or other similar frame or frame-like support structure. Frame members, in some embodiments, can be designed to move between a first condition and one or more other conditions, for example, in the case of a frame that is compactable to a compacted, first condition, and when in this compacted condition, is then expandable to an expanded, second condition. In forms where a frame has the capacity to expand, these frames can include those that are considered self-expanding and those that require at least some manipulation in order to expand.

Frames of this sort and other similar support elements useful in the present invention can be constructed using one or more pieces of superelastic wire or any of a variety of other suitable materials described herein or otherwise known to those skilled in the art including MRI compatible materials. Frames and other similar expandable and non-expandable support members, when utilized in the present invention, may be made from metallic or non-metallic material, or both. The non-metallic material can suitably be a synthetic polymeric material, including for example bioresorbable and/or non-bioresorbable plastics. Materials commonly used in medical device construction include biologically compatible metals, e.g., stainless steel, titanium, tantalum, gold, platinum, copper and the like, as well as alloys of these metals; synthetic polymeric materials; low shape memory plastic; a shape-memory plastic or alloy, such as nitinol; and the like.

In certain forms, a resilient frame member can be provided in a relaxed condition. The frame can then be deformed (e.g., collapsed, compressed, etc.) from this relaxed, first condition to a deformed, second condition and held there. In this deformed, second condition, the resilient frame is then poised to essentially return to its relaxed, first condition. Illustratively, a frame can be compressed into a compressed condition (e.g., by folding one or more times and/or rolling portions of the frame) for positioning in a delivery device lumen having a relatively smaller diameter than that which the frame could otherwise fit in its relaxed condition. In this compressed condition, the frame then has the ability to self-expand essentially back to its prior, relaxed condition upon being removed from the delivery device lumen. In other embodiments, frame members and other frame-like elements exhibit little or no resiliency.

In some instances, a frame element will be urged to expand by another device component exerting force on the frame element as the component expands. This can be made to occur with both self expanding and non-self expanding frame elements. Frames can be provided and delivered in a contracted state, and then expanded upon the application of a force, e.g. an outward radial force, to the frame. Illustratively, an outward force can be provided by an expandable material positioned in and/or around a frame structure. Frame structures which take on a contracted state, but expand in response to a conditional change, e.g., a change in temperature such as may be incurred in a temperature transition from a first temperature below the body temperature of a patient, to the body temperature of the patient, can also be utilized. Frame members having these or other characteristics may be used in embodiments of the present invention.

Turning now to a discussion of occlusive implant materials, illustrative such materials can include any suitable biocompatible material. Generally, the occlusion materials may include synthetic materials or reconstituted or naturally-derived collagenous materials. Thus, inventive devices can utilize one or more of a variety of synthetic polymeric materials including but not limited to bioresorbable and/or non-bioresorbable plastics. Bioresorbable, or bioabsorbable polymers that may be used include, but are not limited to, poly(L-lactic acid), polycaprolactone, poly(lactide-co-glycolide), poly(hydroxybutyrate), poly(hydroxybutyrate-co-valerate), polydioxanone, polyorthoester, polyanhydride, poly(glycolic acid), poly(D,L-lactic acid), poly(glycolic acid-co-trimethylene carbonate), polyhydroxyalkanaates, polyphosphoester, polyphosphoester urethane, poly(amino acids), cyanoacrylates, poly(trimethylene carbonate), poly(iminocarbonate), copoly(ether-esters) (e.g., PEO/PLA), polyalkylene oxalates, and polyphosphazenes. These or other bioresorbable materials may be used, for example, where only a temporary blocking or closure function is desired, and/or in combination with non-bioresorbable materials where only a temporary participation by the bioresorable material is desired.

Non-bioresorbable, or biostable polymers that may be used include, but are not limited to, polytetrafluoroethylene (PTFE) (including expanded PTFE), polyethylene terephthalate (PET), polyurethanes, silicones, and polyesters and other polymers such as, but not limited to, polyolefins, polyisobutylene and ethylene-alphaolefin copolymers; acrylic polymers and copolymers, vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile, polyvinyl ketones; polyvinyl aromatics, such as polystyrene, polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins, polycarbonates; polyoxymethylenes; polyimides; polyethers; epoxy resins, polyurethanes; rayon; and rayon-triacetate.

As well, inventive devices can incorporate biocompatible materials derived from a number of biological polymers, which can be naturally occurring or the product of in vitro fermentation, recombinant genetic engineering, and the like. Purified biological polymers can be appropriately formed into a substrate by techniques such as weaving, knitting, casting, molding, and extrusion. Suitable biological polymers include, without limitation, collagen, elastin, keratin, gelatin, polyamino acids, polysaccharides (e.g., cellulose and starch) and copolymers thereof.

Biocompatible materials that are at least bioresorbable will provide advantage in certain embodiments of the invention, with materials that are bioremodelable and promote cellular invasion and ingrowth providing particular advantage. Illustratively, remodelable materials may be used in this context to promote cellular growth within the occlusive materials to promote the closure of an occluded passageway.

Bioremodelable materials of the invention can be provided by collagenous extracellular matrix (ECM) materials possessing biotropic properties, including in certain forms angiogenic collagenous ECM materials. For example, suitable collagenous materials include ECM materials, such as submucosa, renal capsule membrane, dermal collagen, dura mater, pericardium, serosa, facia lata, peritoneum, or basement membrane layers including liver basement membrane. The preferred medical graft products of the invention will include submucosa, such as submucosa derived from a warm-blooded vertebrate. Suitable submucosa materials for these purposes include, for instance, intestinal submucosa, including small intestinal submucosa, stomach submucosa, urinary bladder submucosa, and uterine submucosa. Mammalian submucosa materials are preferred. In particular, submucosa materials derived from animals raised for meat or other product production, e.g. pigs, cattle or sheep, will be advantageous. Porcine submucosa provides a particularly preferred material for use in the present invention, especially porcine small intestine submucosa (SIS), more especially porcine small intestine submucosa retaining substantially its native cross-linking.

The submucosa or other ECM material can be derived from any suitable organ or other biological structure, including for example submucosa derived from the alimentary, respiratory, intestinal, urinary or genital tracts of warm-blooded vertebrates. Submucosa useful in the present invention can be obtained by harvesting such tissue sources and delaminating the submucosa from smooth muscle layers, mucosal layers, and/or other layers occurring in the tissue source. For additional information concerning submucosa useful in certain embodiments of the present invention, and its isolation and treatment, reference can be made, for example, to U.S. Pat. Nos. 4,902,508, 5,554,389, 5,993,844, 6,206,931, and 6,099,567.

Submucosa or other ECM materials can be derived from any suitable organ or other tissue source, usually sources containing connective tissues. The ECM materials processed for use in certain embodiments will typically include abundant collagen, most commonly being constituted at least about 80% by weight collagen on a dry weight basis. Such naturally-derived ECM materials will for the most part include collagen fibers that are non-randomly oriented, for instance occurring as generally uniaxial or multi-axial but regularly oriented fibers. When processed to retain native bioactive factors, the ECM material can retain these factors interspersed as solids between, upon and/or within the collagen fibers. Particularly desirable naturally-derived ECM materials for use in embodiments of the invention will include significant amounts of such interspersed, non-collagenous solids that are readily ascertainable under light microscopic examination. Such non-collagenous solids can constitute a significant percentage of the dry weight of the ECM material in certain inventive embodiments, for example at least about 1%, at least about 3%, and at least about 5% by weight in various embodiments of the invention.

The submucosa or other ECM material used in illustrative embodiments may also exhibit an angiogenic character and thus be effective to induce angiogenesis in a host engrafted with the material. In this regard, angiogenesis is the process through which the body makes new blood vessels to generate increased blood supply to tissues. Thus, angiogenic materials, when contacted with host tissues, promote or encourage the formation of new blood vessels. Methods for measuring in vivo angiogenesis in response to biomaterial implantation have recently been developed. For example, one such method uses a subcutaneous implant model to determine the angiogenic character of a material. See, C. Heeschen et al., Nature Medicine 7 (2001), No. 7, 833-839. When combined with a fluorescence microangiography technique, this model can provide both quantitative and qualitative measures of angiogenesis into biomaterials. C. Johnson et al., Circulation Research 94 (2004), No. 2, 262-268.

As prepared and used, the submucosa material or any other ECM material may optionally retain and/or include growth factors or other bioactive components native to the source tissue. For example, the submucosa or other ECM material may include one or more growth factors such as basic fibroblast growth factor (FGF-2), transforming growth factor beta (TGF-beta), epidermal growth factor (EGF), and/or platelet derived growth factor (PDGF). As well, submucosa or other ECM material used in embodiments of the invention may include other biological materials such as heparin, heparin sulfate, hyaluronic acid, fibronectin and the like. Thus, generally speaking, the submucosa or other ECM material may include a bioactive component that induces, directly or indirectly, a cellular response such as a change in cell morphology, proliferation, growth, protein or gene expression. In certain preferred embodiments of the invention, the ECM material will exhibit the capacity to promote angiogenesis.

Further, in addition or as an alternative to the inclusion of native bioactive components, non-native bioactive components such as those synthetically produced by recombinant technology or other methods, may be incorporated into the submucosa or other ECM material. These non-native bioactive components may be naturally-derived or recombinantly produced proteins that correspond to those natively occurring in the ECM material, but perhaps of a different species (e.g. human proteins applied to collagenous ECMs from other animals, such as pigs). The non-native bioactive components may also be drug substances. Illustrative drug substances that may be incorporated into and/or onto the ECM material can include, for example, antibiotics and/or thrombus-promoting substances such as blood clotting factors, e.g. thrombin, fibrinogen, and the like. These substances may be applied to the ECM material as a premanufactured step, immediately prior to the procedure (e.g. by soaking the material in a solution containing a suitable antibiotic such as cefazolin), or during or after engraftment of the ECM material within the patient.

Submucosa or other ECM materials used in embodiments of the invention are preferably highly purified, for example, as described in U.S. Pat. No. 6,206,931 to Cook et al. Thus, preferred ECM material will exhibit an endotoxin level of less than about 12 endotoxin units (EU) per gram, more preferably less than about 5 EU per gram, and most preferably less than about 1 EU per gram. As additional preferences, the submucosa or other ECM material may have a bioburden of less than about 1 colony forming units (CFU) per gram, more preferably less than about 0.5 CFU per gram. Fungus levels are desirably similarly low, for example less than about 1 CFU per gram, more preferably less than about 0.5 CFU per gram. Nucleic acid levels are preferably less than about 5 µg/mg, more preferably less than about 2

µg/mg, and virus levels are preferably less than about 50 plaque forming units (PFU) per gram, more preferably less than about 5 PFU per gram. The ECM material used in embodiments of the invention is preferably disinfected with an oxidizing agent, particularly a peracid, such as peracetic acid. These and additional properties of submucosa or other ECM materials taught in U.S. Pat. No. 6,206,931 may be characteristic of the submucosa used in aspects of the present invention.

In certain aspects, the invention utilizes an occluding device that includes a multilaminate material. Such multilaminate materials can include a plurality of ECM material layers bonded together, a plurality of non-ECM materials bonded together, or a combination of one or more ECM material layers and one or more non-ECM material layers bonded together. To form a multilaminate ECM material, for example, two or more ECM segments are stacked, or one ECM segment is folded over itself at least one time, and then the layers are fused or bonded together using a bonding technique, such as chemical cross-linking or vacuum pressing during dehydrating conditions. An adhesive, glue or other bonding agent may also be used in achieving a bond between material layers. Suitable bonding agents may include, for example, collagen gels or pastes, gelatin, or other agents including reactive monomers or polymers, for example cyanoacrylate adhesives. As well, bonding can be achieved or facilitated between ECM material layers using chemical cross-linking agents such as those described above. A combination of one or more of these with dehydration-induced bonding may also be used to bond ECM material layers to one another. Using multilaminate materials can add to the column strength of an implant, or a portion thereof.

A variety of dehydration-induced bonding methods can be used to fuse ECM portions of the bioremodelable material. In one preferred embodiment, the multiple layers of ECM material are compressed under dehydrating conditions. The term "dehydrating conditions" can include any mechanical or environmental condition which promotes or induces the removal of water from the ECM material. To promote dehydration of the compressed ECM material, at least one of the two surfaces compressing the matrix structure can be water permeable. Dehydration of the ECM material can optionally be further enhanced by applying blotting material, heating the matrix structure or blowing air, or other inert gas, across the exterior of the compressing surfaces. One particularly useful method of dehydration bonding ECM materials is lyophilization, e.g. freeze-drying or evaporative cooling conditions.

Another method of dehydration bonding comprises pulling a vacuum on the assembly while simultaneously pressing the assembly together. This method is known as vacuum pressing. During vacuum pressing, dehydration of the ECM materials in forced contact with one another effectively bonds the materials to one another, even in the absence of other agents for achieving a bond, although such agents can be used while also taking advantage at least in part of the dehydration-induced bonding. With sufficient compression and dehydration, the ECM materials can be caused to form a generally unitary ECM structure.

It is sometimes advantageous to perform drying operations under relatively mild temperature exposure conditions that minimize deleterious effects upon the ECM materials of the invention, for example native collagen structures and potentially bioactive substances present. Thus, drying operations conducted with no or substantially no duration of exposure to temperatures above human body temperature or slightly higher, say, no higher than about 38° C., will preferably be used in some forms of the present invention. These include, for example, vacuum pressing operations at less than about 38° C., forced air drying at less than about 38° C., or either of these processes with no active heating—at about room temperature (about 25° C.) or with cooling. Relatively low temperature conditions also, of course, include lyophilization conditions.

Turning now to a discussion of three-dimensionally stable materials that can be formed into occlusive constructs for use in aspects of the invention, such materials may include any suitable biocompatible sponge or foam material. Illustrative sponge or foam matrices will generally comprise porous, three-dimensionally stable bodies formed from suitable biocompatible matrix materials. For example, suitable biocompatible matrix materials include naturally-occurring polymers and/or synthetic polymers. More preferred sponge compositions of the invention will comprise collagen as a matrix-forming material, either alone or in combination with one or more other matrix forming materials. In general, sponge matrices useful in embodiments of the invention can be formed by providing a liquid solution or suspension of a matrix-forming material, and causing the material to form a porous three-dimensionally stable structure; however, a sponge or foam material can be formed using any suitable formation method, as is known in the art.

Illustratively, in the formation of a collagenous sponge or foam material, a collagen solution or suspension can be prepared. The collagen may be derived from mammalian or other animal sources, for example, bovine, porcine or human sources, and desirably is derived from remodelable ECM materials as discussed herein. Synthetically-derived collagen may also be used. The determination of suitable collagen concentrations in the solution will be within the purview of those skilled in the art, with concentration ranges of about 0.05 g/ml to about 0.2 g/ml being typical.

Digestion of the collagen to form the collagen solution is usually carried out under acidic conditions, starting with ground, minced or otherwise comminuted collagen-containing tissue. Optionally, enzymatic digestion may be utilized using known enzymes for this purpose such as pepsin, trypsin, and/or papain. After digestion, the enzymes can be removed by suitable, known techniques.

The collagenous solution and/or suspension can be employed as a moldable or castable material in the formation of the foam or sponge. The cast material can be dried directly without chemical crosslinking or can be crosslinked with a suitable crosslinking agent and then dried. Illustrative crosslinking agents for these purposes include glutaraldehyde, formaldehyde, carbodiimides, UV irradiation, or other crosslinking agents. In preferred embodiments of the invention, the crosslinking agent will contain polar groups that impart a hydrophilic character to the final sponge matrix material. Desirably, a polyepoxide crosslinker is utilized for this purpose, especially a polyglycidyl ether compound. Suitable such compounds include ethylene glycol diglycidyl ether, available under the trade name Denacol EX810 from Nagese Chemical Co., Osaka, Japan, and glycerol polyglycidyl ether available under the trade name Denacol EX313 also from Nagese Chemical Co. Typically, polyglycidyl ethers or other polyepoxide compounds utilized in the invention will have from 2 to about 10 epoxide groups per molecule. The use of such epoxides and/or other crosslinking agents which impart polar groups and a hydrophilic character to the resulting matrix will provide for good wetability and rapid hydration and expansion of closure devices of the invention.

Preferred sources of collagen for forming sponge matrices include extracellular matrix materials as discussed above, such as collagenous submucosal tissues, and other collagenous basement membrane materials. These include, for example, small intestinal submucosa, stomach submucosa, urinary bladder submucosa, liver basement membrane, and other basement membrane materials. For additional information as to these collagenous matrix materials and their preparation, reference can be made for example to U.S. Pat. Nos. 4,511,653, 4,902,508, 4,956,178, 5,554,389, and 6,099,567, and International Publication Nos. WO9825637 and WO9822158, each of which is hereby incorporated herein by reference in its entirety. In forming sponge matrices, these materials are preferably processed and utilized under conditions which retain their favorable growth properties. This may include, for example, processing under conditions in which native proteins and/or other materials, for instance biotropic agents, are retained in their bioactive form. For example, the collagen sources, and resulting sponge matrices, may include active native substances such as one or more growth factors, e.g. basic fibroblast growth factor (FGF-2); transforming growth factor beta (TGF-beta); epidermal growth factor (EFG); platelet derived growth factor (PDGF); and/or other substances such as glycosaminoglycans (GAGs); and/or fibronectin (FN).

Sponge matrix materials can be highly expandable when wetted, so as to achieve an expanded configuration. Illustratively, expandable sponge materials can exhibit the capacity to expand at least 100% by volume, more preferably at least about 200% by volume, and typically in the range of about 300% by volume to about 1000% by volume, when wetted to saturation with deionized water. Sponge materials used in the invention can also exhibit advantageous rates of expansion, achieving volume expansions as noted above in less than about 10 seconds, more preferably less than about 5 seconds, when immersed in deionized water.

Highly compact, dense sponge matrices can be prepared by first hydrating or otherwise wetting a porous sponge matrix, and then compressing and drying the element. Such preparative processes generally provide a more dense, rigid and stably compressed sponge matrix than processes such as simple compaction of the dry sponge matrix. Drying can be conducted sufficiently to stabilize the sponge matrix. For example, preferred drying procedures will reduce the liquid (e.g. water) content of the matrix to less than about 20% by weight, more preferably less than about 10% by weight. Compression forces can be applied so as to achieve a final density and/or desirable configuration, and can be applied in one, two or three dimensions, including radially. The drying of the compacted element can involve lyophilization (or freeze drying) or vacuum drying at ambient or elevated temperatures. When processed in this fashion, upon removal of the compaction force, the sponge matrix is stabilized structurally and remains in its highly dense and compacted state until contacted with a liquid susceptible to absorption by the matrix, for example body fluids. The pores of the matrix are thereby stably retained at a volume substantially reduced from their maximum volume, but return to a partially or fully expanded state when the matrix material is wetted.

Compressed sponge matrices forming occlusive bodies can be highly dense, typically having densities of at least about 0.05 g/cm3, preferably in the range of about 0.05 g/cm3 to about 0.2 g/cm3, and more preferably about 0.075 g/cm3 to about 0.2 g/cm3. The compacted sponge matrix can have sufficient rigidity to be deployed by passage through bodily vessels, needles, catheters or sheaths, such as by utilizing a push rod or other pusher element to force the sponge matrix body through the needle and/or catheter cannula for example. Expanded sponge densities (dry) will generally be less than the corresponding compacted densities. Typical expanded densities (dry) will range from about 0.01 g/cm3 to about 0.1 g/cm3, more preferably about 0.02 g/cm3 to about 0.07 g/cm3.

Compressed sponge materials may also contain agents which promote further retention of the compressed, high density form of the matrices. These may include for example starch, cellulose, sugars such as dextrose, or glycerin. Such agents can optionally be included in the liquid (preferably aqueous) used to hydrate or otherwise wet the sponge prior to compaction and drying. For additional information concerning foam or sponge form materials that can be useful in embodiments of the invention, reference can be made, for example, to U.S. Pat. App. Pub. No. 2003/0013989.

In additional embodiments, occlusion devices of the invention can be made from ECM's or other collagenous materials that have been subjected to processes that expand the materials. In certain forms, such expanded materials can be formed by the controlled contact of an ECM material with one or more alkaline substances until the material expands, and the isolation of the expanded material. Illustratively, the contacting can be sufficient to expand the ECM material to at least 120% of (i.e. 1.2 times) its original bulk volume, or in some forms to at least about two times its original volume. Thereafter, the expanded material can optionally be isolated from the alkaline medium, e.g. by neutralization and/or rinsing. The collected, expanded material can be used in any suitable manner in the preparation of a graft device. Illustratively, the expanded material can be enriched with bioactive components, dried, and/or molded, etc., in the formation of a graft construct of a desired shape or configuration. In certain embodiments, a dried graft construct formed with the expanded ECM material can be highly compressible (or expandable) such that the material can be compressed for delivery, such as from within the lumen of a cannulated delivery device, and thereafter expand upon deployment from the device so as to become anchored within a patient and/or cause closure of a bodily segment within the patient.

Expanded collagenous or ECM materials can be formed by the controlled contact of a collagenous or ECM material with an aqueous solution or other medium containing sodium hydroxide. Alkaline treatment of the material can cause changes in the physical structure of the material that in turn cause it to expand. Such changes may include denaturation of the collagen in the material. In certain embodiments, it is preferred to expand the material to at least about three, at least about four, at least about 5, or at least about 6 or even more times its original bulk volume. The magnitude of the expansion is related to several factors, including for instance the concentration or pH of the alkaline medium, exposure time, and temperature used in the treatment of the material to be expanded.

ECM materials that can be processed to make expanded materials can include any of those disclosed herein or other suitable ECM's. Typical such ECM materials will include a network of collagen fibrils having naturally-occurring intramolecular cross links and naturally-occurring intermolecular cross links. Upon expansion processing as described herein, the naturally-occurring intramolecular cross links and naturally-occurring intermolecular cross links can be retained in the processed collagenous matrix material sufficiently to maintain the collagenous matrix material as an intact collagenous sheet material; however, collagen fibrils in the collagenous sheet material can be denatured, and the collagenous sheet material can have an alkaline-processed thickness that is greater than the thickness of the starting material, for example at least 120% of the original thickness, or at least twice the original thickness.

Illustratively, the concentration of the alkaline substance for treatment of the remodelable material can be in the range of about 0.5 to about 2 M, with a concentration of about 1 M being more preferable. Additionally, the pH of the alkaline substance can in certain embodiments range from about 8 to about 14. In preferred aspects, the alkaline substance will have a pH of from about 10 to about 14, and most preferably of from about 12 to about 14.

In addition to concentration and pH, other factors such as temperature and exposure time will contribute to the extent of expansion, as discussed above. In this respect, in certain variants, the exposure of the collagenous material to the alkaline substance is performed at a temperature of about 4 to about 45° C. In preferred embodiments, the exposure is performed at a temperature of about 25 to about 40° C., with 37° C. being most preferred. Moreover, the exposure time can range from at least about one minute up to about 5 hours or more. In some embodiments, the exposure time is about 1 to about 2 hours. In a particularly preferred embodiment, the collagenous material is exposed to a 1 M solution of NaOH having a pH of 14 at a temperature of about 37° C. for about 1.5 to 2 hours. Such treatment results in collagen denaturation and a substantial expansion of the remodelable material. Denaturation of the collagen matrix of the material can be observed as a change in the collagen packing characteristics of the material, for example a substantial disruption of a tightly bound collagenous network of the starting material. A non-expanded ECM or other collagenous material can have a tightly bound collagenous network presenting a substantially uniform, continuous surface when viewed by the naked eye or under moderate magnification, e.g. 100× magnification. Conversely, an expanded collagenous material can have a surface that is quite different, in that the surface is not continuous but rather presents collagen strands or bundles in many regions that are separated by substantial gaps in material between the strands or bundles when viewed under the same magnification, e.g. about 100×. Consequently, an expanded collagenous material typically appears more porous than a corresponding non-expanded collagenous material. Moreover, in many instances, the expanded collagenous material can be demonstrated as having increased porosity, e.g. by measuring for an increased permeability to water or other fluid passage as compared to the non-treated starting material. The more foamy and porous structure of an expanded ECM or other collagenous material can allow the material to be cast or otherwise prepared into a variety of three-dimensionally stable shapes for use in the preparation of medical materials and devices. It can further allow for the preparation of constructs that are highly compressible and which expand after compression. Such properties can be useful, for example, when the prepared graft construct is to be compressed and loaded into a deployment device (e.g. a lumen thereof) for delivery into a patient, and thereafter deployed to expand at the implant site.

After such alkaline treatments, the material can be isolated from the alkaline medium and processed for further use. Illustratively, the collected material can be neutralized and/or rinsed with water to remove the alkalinity from the material, prior to further processing of the material to form a graft construct.

A starting ECM material (i.e., prior to treatment with the alkaline substance) can optionally include a variety of bioactive or other non-collagenous components including, for example, growth factors, glycoproteins, glycosaminoglycans, proteoglycans, nucleic acids, and lipids. Treating the material with an alkaline substance may reduce the quantity of one, some or all of such non-collagenous components contained within the material. In certain embodiments, controlled treatment of the remodelable material with an alkaline substance will be sufficient to create a remodelable collagenous material which is substantially devoid of nucleic acids and lipids, and potentially also of growth factors, glycoproteins, glycosaminoglycans, and proteoglycans.

In certain embodiments, one or more bioactive components, exogenous or endogenous, for example, similar to those removed from an expanded material during alkaline processing, can be returned to the material. For example, an expanded material can include a collagenous material which has been depleted of nucleic acids and lipids, but which has been replenished with growth factors, glycoproteins, glycosaminoglycans, and/or proteoglycans. These bioactive components can be returned to the material by any suitable method. For instance, in certain forms a tissue extract, such as is discussed in U.S. Pat. No. 6,375,989 which is hereby incorporated herein by reference in its entirety, containing these components can be prepared and applied to an expanded collagenous material. In one embodiment, the expanded collagenous material can be incubated in a tissue extract for a sufficient time to allow bioactive components contained therein to associate with the expanded collagenous material. The tissue extract may, for example, be obtained from non-expanded collagenous tissue of the same type used to prepare the expanded material. Other means for returning or introducing bioactive components to an expanded remodelable collagenous material include spraying, impregnating, dipping, etc. as known in the art. By way of example, an expanded collagenous material may be modified by the addition of one or more growth factors such as basic fibroblast growth factor (FGF-2), transforming growth factor beta (TGF beta), epidermal growth factor (EGF), platelet derived growth factor (PDGF), and/or cartilage derived growth factor (CDGF). As well, other biological components may be added to an expanded collagenous material, such as heparin, heparin sulfate, hyaluronic acid, fibronectin and the like. Thus, generally speaking, an expanded collagenous material may include a bioactive component that induces, directly or indirectly, a cellular response such as a change in cell morphology, proliferation, growth, protein or gene expression.

Expanded collagenous materials can be used to prepare a wide variety of occlusive devices. Methods for preparing such occlusive devices can include contacting an ECM or other collagenous starting material with an alkaline substance in an amount effective to expand the material, casting or otherwise forming the expanded collagenous material into an occlusive shape (e.g. an elongate tube or cylinder), and lyophilizing the expanded material to form a dried occlusive device.

Implantable devices can be any suitable length and will generally be of sufficient dimension to achieve occlusion of the desired stretch of vascular vessel, either alone or in combination with other similar or differing devices. In certain embodiments, a device, in implanted form, will have a length of at least about 0.4 cm, and in many situations will have a length ranging from about 1 cm to about 30 cm, more typically from about 2 cm to about 15 cm. Indeed, for preferred occlusion procedures involving a significant stretch of an artery or vein, one or more occlusion devices having a total length greater than 30 cm will be used. Illustratively, in the occlusion of the greater saphenous vein in human adolescents or adults, one or more occlusion devices having a total length of at least about 40 cm or 50 cm can be used.

While discussions above focus upon occluding the greater saphenous vein via access at the knee level, the greater saphenous vein may also be accessed at a lower level, e.g. near the ankle. During such access, any or all of the saphenous vein occurring between the ankle and the sapheno-femoral junction may be subjected to occlusion. Other veins in the leg(s) that may be involved in the varicose vein condition may also be occluded, alternatively or in addition to the greater saphenous vein. For example, the lesser saphenous vein, or varicose veins themselves, may be occluded and obliterated in accordance with the invention. Further, other veins or arteries in the leg(s) or elsewhere in the body may be occluded within the scope of the present invention.

In additional embodiments, the present invention provides medical products that include means or devices as described herein for delivering vascular implants into and otherwise providing occlusion in the vasculature, and written materials including instructions for use of the means or devices to deliver vascular implants into and otherwise provide occlusion in the vasculature. The products can include the means or devices packaged together with the instructions, e.g. in sterile medical packaging. Related embodiments of the invention include methods for distributing such means or devices, or otherwise conducting business, which include distributing such means or devices for delivering vascular implants into and otherwise providing occlusion in the vasculature, and also distributing information relating the use of such means or devices for delivering vascular implants into and otherwise providing occlusion in the vasculature. Such information can be distributed packaged with the means or device, or separately, e.g. including information or instructions available on a communication network, including a global computer communication network such as the internet.

The present invention also provides, in certain aspects, a line of medical products, wherein a medical product of the invention includes one or more devices, apparatuses or systems of the invention in a sealed package. In some forms of the invention, medical products are provided that include one or more occlusion devices such as any of those described herein, and potentially also a suitable delivery apparatus or other delivery instrumentation, enclosed within sterile medical packaging. Illustratively, such a medical product can have packaging including a backing layer and a front film layer that are joined by a boundary of pressure-adhesive as is conventional in medical packaging, wherein the contents of the packaging are sealed between the backing layer and front film layer. Sterilization of such a medical product may be achieved, for example, by irradiation, ethylene oxide gas, or any other suitable sterilization technique, and the materials and other properties of the medical packaging will be selected accordingly.

Additionally, the package can include indicia to communicate the contents of the package to a person, machine, computer, and/or electronic device. Such indicia may include the dimensions of, the type of materials used to form, and/or other useful information regarding the contents of the package. In certain embodiments, the contents are packaged for sale with instructions for use. For example, in certain preferred embodiments, a medical product includes at least one occlusion device and delivery instrumentation sealed within a sterile package, wherein the packaging can have visible indicia identifying the contents as suitable for providing occlusion in the vasculature, and/or can contain or otherwise be associated with printed materials identifying the contents as such and including information concerning their use.

All publications and patent applications cited in this specification are herein incorporated by reference as if each individual publication or patent application were specifically and individually indicated to be incorporated by reference. Further, any theory, mechanism of operation, proof, or finding stated herein is meant to further enhance understanding of the present invention, and is not intended to limit the present invention in any way to such theory, mechanism of operation, proof, or finding. While the invention has been illustrated and described in detail in the drawings and foregoing description, the same is to be considered as illustrative and not restrictive in character, it being understood that only selected embodiments have been shown and described and that all equivalents, changes, and modifications that come within the spirit of the inventions as defined herein or by the following claims are desired to be protected.

What is claimed is:

1. A medical product for occluding a vascular vessel, the medical product comprising:
    a vascular implant suitable for transluminal vascular delivery to a vascular vessel site, the implant comprising:
        a first expandable occluding member, wherein the first expandable occluding member is compressible to permit delivery through the vasculature to a first location within the vascular vessel site, and wherein the first expandable occluding member is expandable to block blood flow through the vessel at the first location;
        a second expandable occluding member spaced from the first expandable occluding member, wherein the second expandable occluding member is compressible to permit delivery through the vasculature to a second location within the vascular vessel site spaced from the first location, and wherein the second expandable occluding member is expandable to block blood flow through the vessel at the second location; and
        an intermediate segment extending between the first expandable occluding member and the second expandable occluding member, said intermediate segment comprising a flexible material having an interior region for receipt of a fill material; and
        a fill material for filling at least part of the interior region such that filling the interior region with said fill material will force the flexible material towards a wall of the vascular vessel.

2. The medical product of claim 1, wherein at least one of the first expandable occluding member and the second expandable occluding member is comprised of a naturally derived material.

3. The medical product of claim 1, wherein at least one of the first expandable occluding member and the second expandable occluding member is comprised of a non-naturally derived material.

4. The medical product of claim 1, wherein at least one of the first expandable occluding member and the second expandable occluding member is comprised of a remodelable material.

5. The medical product of claim 1, wherein at least one of the first expandable occluding member and the second expandable occluding member is self-expandable.

6. The medical product of claim 1, wherein the fill material includes a sclerosant.

7. The medical product of claim 1, wherein the fill material includes a collagen-containing material.

8. The medical product of claim 1, wherein the intermediate segment is comprised of a naturally derived material.

9. The medical product of claim 1, wherein the intermediate segment is comprised of a non-naturally derived material.

10. The medical product of claim 1, wherein the intermediate segment has a plurality of passages therein through which fill material can pass to exit said interior region.

11. The medical product of claim 10, wherein the intermediate segment comprises a tube having a first end and a second end.

12. The medical product of claim 11, wherein the first expandable occluding member and the second expandable occluding member each comprise an expandable sponge material sized and configured to fill and occlude the vessel, the first expandable occluding member attached to the first end of the tube and the second expandable occluding member attached to the second end of the tube.

13. The medical product of claim 12, wherein the fill material comprises an injectable sclerosant.

14. The medical product of claim 1, wherein said vascular implant is deliverable through a delivery catheter.

15. The medical product of claim 14, also comprising an injection tube configured to deliver said fill material to said interior region.

16. The medical product of claim 15, wherein said injection tube extends through said second expandable member, said injection tube having a distal region, said distal region having an opening in fluid communication with said interior region.

17. A medical product for occluding a vascular vessel, the medical product comprising:
an implant having a first end portion, a second end portion and a wall of flexible material extending therebetween so as to provide a fillable implant body between said first end portion and said second end portion, the fillable implant body comprising a tubular segment having an interior region such that filling the interior region with a fill material forces said wall of flexible material to expand outwardly, the first end portion comprising a first expandable member, and the second end portion comprising a second expandable member, wherein the first expandable member and the second expandable member are each compressible to permit transluminal vascular delivery to a vascular vessel site, and expandable at the site so as to position the respective end portion in the vessel to block flow through the vessel; and
an injection tube extending through said second expandable member and into said interior region, said injection tube having a distal opening in fluid communication with said interior region.

18. The medical product of claim 17, wherein the wall of flexible material is bonded to the first expandable member and the second expandable member.

19. The medical product of claim 17, wherein at least one of the first expandable member and the second expandable member comprises a frame.

20. The medical product of claim 19, wherein the frame is self-expandable.

21. The medical product of claim 17, wherein at least one of the first expandable member and the second expandable member comprises a sponge material.

22. The medical product of claim 17, wherein the wall of flexible material includes a generally cylindrical portion.

23. A medical product for occluding a vascular vessel, the medical product comprising:
a vascular implant suitable for transluminal vascular delivery to a vascular vessel site, the implant comprising:
a tubular segment having a first end and a second end and including a wall defining an interior region, the wall formed with a compliant sheet material harvested from a collagenous tissue source, the tubular segment deliverable to a vascular vessel site for lining an interior wall of the vessel;
a first expandable occluding member attached to the tubular segment at or near its first end wherein said first expandable member is comprised of a naturally-derived collagenous material, and wherein the first expandable occluding member is compressible to permit delivery through the vasculature and expandable to block blood flow through the vessel.

24. The medical product of claim 23, further comprising an endoluminally advanceable delivery device having a lumen, wherein the vascular implant is removably positioned in the delivery device lumen, and is deployable from the lumen in a vascular vessel.

25. The medical product of claim 23, further comprising a fill material for filling an interior region of the tube.

26. The medical product of claim 25, wherein the tube wall has a plurality of passages therein through which fill material can pass to exit said interior region.

27. The medical product of claim 23, wherein the sheet material comprises an extracellular matrix material.

28. The medical product of claim 27, wherein the extracellular matrix material comprises serosa, pericardium, submucosa, dura mater, peritoneum, or dermal collagen.

29. The medical product of claim 23, also comprising a second expandable occluding member attached to the tubular segment at or near its second end, wherein the first occluding member and the second occluding member are each compressible to permit delivery through the vasculature, and expandable in a vascular vessel to occlude the vessel.

30. A method for occluding a vascular vessel, comprising:
providing a vascular implant as described in claim 1
delivering the vascular implant to the vascular vessel site such that the first expandable occluding member and the second expandable occlusing member expand to block blood flow through the vessel;
providing a fill material for filling the interior region of the intermediate segment; and
filling at least part of the interior region with the fill material.

31. The method of claim 30, wherein said delivering includes:
providing a delivery device having a lumen;
removably positioning the vascular implant in the delivery device lumen;
locating the delivery device in the vascular vessel; and
deploying the vascular implant from the delivery device lumen.

32. The method of claim 30, wherein the intermediate segment has a plurality of passages therein through which fill material can pass to exit the interior region.

33. The method of claim 30, wherein said filling comprises injecting said fill material into said interior region.

34. A method for occluding a vascular vessel, comprising:
providing an endoluminally advanceable delivery device, said delivery device having a lumen communicating with a distal open end, and further having an expandable cuff located at or near said distal end;
providing a vascular implant as described in claim 1, the vascular implant removably positioned in the delivery device lumen, the implant being configured for deployment from the delivery device lumen in the vascular vessel for occluding the vessel:
locating the delivery device in a vascular vessel;
expanding said expandable cuff so as to occlude the vessel at a third vessel location;
deploying the first expandable occluding member from the delivery device lumen such that the first expandable occluding member expands and occludes the vessel at a first vessel location spaced from said third vessel location, thereby forming an occluded vessel segment between the expanded cuff and the expanded first expandable occluding member, the occluded vessel segment containing blood;
evacuating at least part of the blood from the occluded vessel segment through the delivery device lumen; and
deploying the second expandable occluding member from the delivery device lumen such that the second expandable occluding member expands and occludes the vessel at a second vessel location occurring between said first vessel location and said third vessel location.

35. A method for occluding a vascular vessel, comprising:
providing a vascular implant as described in claim 23;
delivering the vascular implant to the vascular vessel site such that the first expandable occluding member expands to block flow through the vessel;
providing a fill material for filling the interior region of the tubular segment; and
filling at least part of the interior region with the fill material.

36. The method of claim 35, also comprising filling the interior region of the tubular segment with a fill material.

37. A method for occluding a vascular vessel, comprising:
providing an endoluminally advanceable delivery device, said delivery device having a lumen communicating with a distal open end, and further having an expandable cuff located at or near said distal end;
providing a vascular implant as described in claim 23, the implant removably positioned in the delivery device lumen, the implant being configured for deployment from the delivery device lumen in the vascular vessel for occluding the vessel;
locating the delivery device in a vascular vessel;
expanding said expandable cuff so as to occlude the vessel at a first vessel location;
deploying the first expandable occluding member from the delivery device lumen such that the first expandable occluding member expands and occludes the vessel at a second vessel location spaced from said first vessel location, thereby forming an occluded vessel segment between the expanded cuff and the expanded first expandable occluding member, the occluded vessel segment containing blood;
evacuating at least part of the blood from the occluded vessel segment through the delivery device lumen; and
deploying the tubular segment from the delivery device lumen.

38. The method of claim 37, also comprising filling the interior region of the tubular segment with a fill material.

* * * * *